US008206720B2

United States Patent
Masignani et al.

(10) Patent No.: US 8,206,720 B2
(45) Date of Patent: Jun. 26, 2012

(54) FUSION PROTEINS COMPRISING CD4 MINIMAL MODULES AND INVASIN POLYPEPTIDES THAT ARE CAPABLE OF BINDING TO THE HIV ENVELOPE AND EXPOSING CRYPTIC NEUTRALIZIATION EPITOPES

(75) Inventors: Vega Masignani, Siena (IT); Maria Scarselli, Siena (IT); Barbara Capecchi, Siena (IT); Victoria Sharma, Orinda, CA (US); Susan W. Barnett, San Francisco, CA (US); Indresh K. Srivastava, Benicia, CA (US); Rino Rappuoli, Castelnuovo Berardenga (IT)

(73) Assignee: Novartis Vaccines & Diagnostics, Inc, Emeryville, CA (US)

( * ) Notice: Subject to any disclaimer, the term of this patent is extended or adjusted under 35 U.S.C. 154(b) by 1157 days.

(21) Appl. No.: 11/597,340

(22) PCT Filed: Jun. 8, 2005

(86) PCT No.: PCT/US2005/022801
§ 371 (c)(1),
(2), (4) Date: Aug. 3, 2007

(87) PCT Pub. No.: WO2006/085959
PCT Pub. Date: Aug. 17, 2006

(65) Prior Publication Data
US 2010/0183653 A1    Jul. 22, 2010

Related U.S. Application Data

(60) Provisional application No. 60/578,211, filed on Jun. 8, 2004, provisional application No. 60/578,151, filed on Jun. 8, 2004.

(51) Int. Cl.
| A61K 39/00 | (2006.01) |
| A61K 39/21 | (2006.01) |
| A61K 38/00 | (2006.01) |
| A61K 39/02 | (2006.01) |
| C07K 1/00 | (2006.01) |

(52) U.S. Cl. ............... 424/192.1; 424/208.1; 424/234.1; 530/300; 530/350

(58) Field of Classification Search .................. None
See application file for complete search history.

(56) References Cited

U.S. PATENT DOCUMENTS 4,708,871 A    11/1987  Geysen
(Continued)

FOREIGN PATENT DOCUMENTS
WO    9419017 A1    9/1994
(Continued)

OTHER PUBLICATIONS

Zettlmeissl, G., et al. 1990. Expression and characterization of human CD4: immunoglobulin fusion domains. DNA Cell Biol. 9(5):347-353.*

(Continued)

*Primary Examiner* — Jeffrey S. Parkin
(74) *Attorney, Agent, or Firm* — Regina Bautista; Helen Lee

(57) ABSTRACT

Fusion proteins comprising CD4 minimal modules that bind to HIV Env polypeptides in a non-CD4 backbone are described. Also described are complexes of these fusion proteins with Env as well as methods of diagnosis, treatment and prevention using the polynucleotides and polypeptides are also provided.

12 Claims, 10 Drawing Sheets

Invasin-CD4 Constructs

A. CD4-D1  191aa — CD4 [15-85], InvA D1 [503-595], InvA [737-751], InvA [584-595]

B. CD4-D2  290aa — InvA D1+D2 [503-694]

C. CD4-D3  391aa — InvA D1+D2+D3  [503-795]

D. CD4-D4  484aa — InvA D1+D2+D3+D4  [503-888]

U.S. PATENT DOCUMENTS

| | | | |
|---|---|---|---|
| 5,518,723 | A | 5/1996 | Devico et al. |
| 5,714,316 | A | 2/1998 | Weiner et al. |
| 5,843,454 | A | 12/1998 | Devico et al. |
| 6,004,781 | A | 12/1999 | Seed et al. |
| 6,030,772 | A | 2/2000 | Devico et al. |
| 6,117,656 | A * | 9/2000 | Seed ............................ 435/69.7 |
| 7,811,580 | B2 | 10/2010 | Barnett et al. |
| 2002/0177551 | A1 | 11/2002 | Terman |
| 2008/0317779 | A1 | 12/2008 | Barnett et al. |
| 2010/0183653 | A1 | 7/2010 | Masignani et al. |

FOREIGN PATENT DOCUMENTS

| | | |
|---|---|---|
| WO | 9604301 A2 | 2/1996 |
| WO | 0039302 A2 | 7/2000 |
| WO | 0039303 A2 | 7/2000 |
| WO | 0130814 A1 | 5/2001 |
| WO | 03020876 A2 | 3/2003 |
| WO | 2004014420 A1 | 2/2004 |
| WO | 2004037847 A2 | 5/2004 |

OTHER PUBLICATIONS

Aullo, P., et al., 1992, A recombinant diptheria toxin related human CD4 fusion protein specifically kills HIV infected cells which express gp120 but selects fusion toxin resistant cells which carry HIV, EMBO J. 11(2):575-583.*

Al-Jaufy, A. Y., et al., 1994, Cytotoxicity of a Shiga toxin A subunit-CD4 fusion protein to human immunodeficiency virus-infected cells, Infect. Immun. 62(3):956-960.*

Wu, H., et al., 1996, Kinetic and structural analysis of mutant CD4 receptors that are defective in HIV gp120 binding, Proc. Natl. Acad. Sci. USA 93:15030-15035.*

Vita et al., (1998) "Novel Miniproteins Engineered by the Transfer of Active Sites to Small Natural Scaffolds", Biopolymers 47: 93-100.

Vita et al., (1999) "Rational engineering of a miniprotein that reproduces the core of the CD4 site interacting with HIV-1 envelope glycoprotein", Proc. Natl. Acad. Sci. USA 96: 13091-96.

Vu et al., (2006) "An Immunoglobulin Fusion Protein Based on the gp120-CD4 Receptor complex Potently Inhibits Human Immunodeficiency Virus Type 1 in Vitro", AIDS Res. Human Retroviruses 22: 477-90.

Weis et al., (1985) "Neutralization of Human T-Lymphotropic Virus Type III by Sera of AIDS and AIDS-Risk Patients", Nature 316: 69-72.

Weis et al., (1986) "Variable and Conserved Neutralization Antigens of Human Immunodeficiency Virus", Nature 324: 572-75.

Wyatt et al., (1995) "Involvement of the V1/V2 Variable Loop Structure in the Exposure of Human Immunodeficiency Virus Type 1 gp120 Epitopes Induced by Receptor Binding", J. Virol. 69: 5723-33.

Wyatt et al., (1998) "The antigenic structure of the HIV gp120 envelope glycoprotein", Nature 393: 705-11.

Xiao, X. et al., (2003) "Purified complexes of HIV-1 envelope glycoproteins with CD4 and CCR5(CXCR4): production, characterization, and immunogenicity", Vaccine 21: 4275-4284.

Zagury et al., (1986) "Long-Term Cultures of HTLV-III-Infected T Cells: A Model of Cytopathology of T-Cell Depletion in AIDS", Science 231: 850-53.

Zhang et al., (1999) "Conformational Changes of gp120 in Epitopes near the CCR5 Binding Site are Induced by CD4 and a CD4 Miniprotein Mimetic", Biochemistry 38: 9405-16.

Zhu et al., (1993) "Genotypic and Phenotypic Characterization of HIV-1 in Patients with Primary Infection", Science, 261: 1179-81.

Cordonnier et al., (Aug. 17, 1989) "Single amino-acid changes in HIV envelope affect viral tropism and receptor binding," Nature., 340(6234): 571-574.

Lasky et al., (Sep. 11, 1987) "Delineation of a region of the human immunodeficiency virus type 1 gp120 glycoprotein critical for interaction with the CD4 receptor," Cell., 50(6): 975-85.

Arthos et al., (1989) "Identification of the Residues in Human CD4 Critical for the Binding of HIV", Cell 57: 469-81.

Ashkenazi, A. et al., (1990) "Mapping the CD4 binding site for human immunodeficiency virus by alanine-scanning mutagenesis", Proc. Natl. Acad. Sci., USA 87: 7150-7154.

Barre-Sinoussi et al., (1983) "Isolation of a T-Lymphotropic Retrovirus from a Patient at Risk for Acquired Immune Deficiency Syndrome (AIDS)", Science 220: 868-71.

Binley et al., (1997) "An Investigation of the High_Avidity Antibody Response to Glycoprotein 120 of Human Immunodeficiency Virus Type 1", AIDS Res. Hum. Retroviruses 13: 1007-15.

Bolognesi et al., (1994) "HIV Vaccine Development: A Progress Report", Ann. Int. Med. 8: 603-11.

Burton, D.R. et al., (2004) "HIV vaccine design and the neutralizing antibody problem", Nat. Immunol., 5(3): p. 233-236.

Burton & Montefiore, (1997) "The antibody response in HIV-1 infection", AIDS 11 (Suppl. A): 587-98.

Clackson & Wells, (1995) "A Hot Spot of Binding Energy in a Hormone-Receptor Interface", Science 267: 383-86.

Dash, B. et al., (1994) "Deletion of a single N-linked glycosylation site from the transmembrane envelope protein of human immunodeficiency virus type 1 stops cleavage and transport of gp160 preventing env-mediated fusion", J. Gen. Virol., 75(6): 1389-1397.

Devico et al., (1995) "Monoclonal Antibodies Raised Against Covalently Crosslinked of Human Immunodeficiency Type 1 gp120 and CD4 Receptor Identify a Novel Complex-Dependent Epitope on gp120", Virol. 211: 583-88.

Devico et al., (1996) "Covalently Crosslinked Complexes of Human Immunodeficiency Virus Type 1 (HIV-1) gp120 and CD4 Receptor Elicit a Neutralizing Immune Response That Includes Antibodies Selective for Primary Virus Isolates", Virology 218: 258-63.

Dey, B. et al., (2003) "Neutralization of human immunodeficiency virus type 1 by sCD4-17b, a single-chain chimeric protein, based on sequential interaction of gp120 with CD4 and coreceptor", J. Virol., 77(5): 2859-2865.

D'Souza et al., (1997) "Evaluation of Monoclonal Antibodies to Human Immunodeficiency Virus Type 1 Promary Isolates by Neutralization Assays: Performance Criteria for Selecting Candidate Antibodies for Clinical Trials", J. Infect. Dis. 75: 56-62.

Fiore et al., (1994) "The Biological Phenotype of HIV-1 is Usually Retained During and After Sexual Transmission", Virol. 204: 297-303.

Fouts et al., "Crosslinked HIV-1 envelope-CD4 receptor complexes elicit broadly cross-reactive neutralizing antibodies in rhesus macaques," Proc Natl Acad Sci U S A. Sep. 3, 2002;99(18):11842-7. Epub Aug. 21, 2002.

Gallo et al., (1984) "Frequent Detection and Isolation of cytopathic Retroviruses (HTL V-III) from Patients with AIDS and at Risk for AIDS", "Serological Analysis of a Subgroup of Human T-Lymphotropic Retroviruses (HTL V-III) Associated with AIDS"; Science 224: 500-03.

Gallo, R.C. et al., (2005) "The end of the beginning of the drive to an HIV-preventive vaccine: A view from over 20 years", The Lancet 366:1894-1898.

Database PIR Entry A03976 (Entry VCLJA2), May 17, 1985.

Gershoni et al., (1993) "HIV Binding to Its Receptor Creates Specific Epitopes for the CD4/gp120 Complex", FASEB J. 7: 1185-87.

Geysen et al., (1984) "Use of peptide synthesis to probe viral antigens for epitopes to a resolution of a single amino acid", Proc. Natl. Acad. Sci., USA 81: 3998-4002.

Geysen et al., (1986) "A Priori Delineation of a Peptide Which Mimics a Discontinuous Antigenic Determinant", Mol. Immunol. 23: 709-15.

Guyader et al., (1987) "Genome Organization and Transactivation of the Human Immunodeficiency Virus Type 2", Nature 326: 662-69.

Haynes et al., (1996) "Toward an Understanding of the Correlates of Protective Immunity to HIV Infection", Science 271: 327-28.

Hu et al., (1992) "Protection of Macaques Against SIV Infection by Subunit Vaccines of SIV Envelope Glycoprotein gp160", Science 255: 456-59.

Javaherian et al., (1989) "Principal neutralizing domain of the human immunodeficiency virus type 1 envelope protein", Proc. Natl. Acad. Sci., USA 86: 6786-72.

Kwong et al., (1998) "Structure of an HIV gp120 envelope glycoprotein in complex with the CD4 receptor and a neutralizing human antibody", Nature 393: 648-59.

Lacasset et al., (1999) "Fusion-Competent Vaccines: Broad Neutralizations of Primary Isolates of HIV", Science 283: 357-62.

Levy et al., (1984) "Isolation of Lymphocytopathic Retroviruses from San Francisco Patients with AIDS", Science 225: 840-42.

Lu, S. et al., (1998) "Immunogenicity of DNA vaccines expressing human immunodeficiency virus type 1 envelope glycoprotein with and without deletions in the V1/2 and V3 regions", AIDS Res. Human Retrovir., 14(2): 151-5.

Martin et al., (2003) "Rational Design of a CD4 Mimic that Inhibits HIV-1 Entry and Exposes Cryptic Neutralization Epitopes"; Nat. Biotech. 21: 71-76.

Mascola et al., (1996) "Immunization with Envelope Subunit Vaccine Products Elicits Neutralizing Antibodies against Laboratory-Adapted but not Primary Isolates of Human Immunodeficiency Virus Type 1", J. Infect. Dis. 173: 340-48.

Matsushita et al., (1988) "Characterization of a Human Immunodeficiency Virus Neutralizing Monoclonal Antibody and Mapping of the Neutralizing Epitope", J. Virol. 62: 2107-44.

Matthews, (1986) "Restricted neutralization of divergent human T-lymphotropic virus type III isolates by antibodies to the major envelope glycoprotein", Proc. Natl. Acad. Sci. USA 83: 9709-13.

Montefiori & Evans, (1999) "Toward an HIV Type 1 Vaccine that Generates Potent, Broadly Cross-Reactive Neutralizing Antibodies", AIDS Res. Hum. Retroviruses 15: 689-98.

Nara et al., (1988) "Purified Envelope Glycoproteins from Human Immunodeficiency Virus Type 1 Variants Induce Individual, Type-Specific Neutralizing Antibodies", J. Virol. 62: 2622-28.

Palker et al., (1988) "Type-specific neutralization of the human immunodeficiency virus with antibodies to env-encoded synthetic peptides", Proc. Natl. Acad. Sci. USA 85: 1932-36.

Putney et al., (1986) "HTLV-III/LAV-Neutralizing Antibodies to an E. coli-Produced Fragment of the Virus Envelope", Science 234: 1392-95.

Ratner et al., (1985) "Complete Nucleotide of the AIDS Virus, HTLV-III", Nature 313: 277-84.

Rizzuto et al., (1998) "A Conserved HIV gp120 Glycoprotein Structure Involved in Chemokine Receptor Binding", Science 280: 1949-53.

Robert-Guroff et al., (1985) "HTLV-III-Neutralizing Antibodies in Patients with AIDS and AIDS-Related Complex", Nature 316: 72-73.

Rushe et al., (1988) "Antibodies that inhibit fusion of human immunodeficiency virus-infected cells bind a 24-amino acid sequence of the viral envelope, gp120", Proc. Natl. Acad. Sci. USA 85: 3198-202.

Ryu et al., (1994) "Structures of an HIV and MHC binding fragment from human CD4 as refined in two crystal lattices", Structure 2: 59-74.

Sanchez-Pescador et al., (1985) "Nucleotide Sequence and Expression of an AIDS-Associated Retrovirus (ARV-2)", Science 227: 484-92.

Siegal et al., (1981) "Severe Acquired Immunodeficiency in male Homosexuals, manifested by Chronic Perianal Ulcerative Herpes Simplex Lesions", N. Engl. J. Med. 305: 1439-44.

Stamatatos & Cheng-Mayer, (1998) "An Envelope Modification That Renders a primary, neutralization-Resistant Clade B Human Immunodeficiency Virus Type 1 Isolate Highly Susceptible to Neutralization by Sera from Other Clades", J. Virol. 72: 7840-45.

Stamatatos et al., (1998) "Effect of major Deletions in the V1 and V2 Loops of a Macrophage-Tropic HIV Type 1 Isolate on Viral Envelope Structure, Cell Entry and Replication", Aids Res. Hum. Retroviruses 14, 1129-39.

Sullivan et al., (1998) "Determinants of Human Immunodeficiency Virus Type 1 Envelope Clycoprotein Activation by Soluble CD4 and Monoclonal Antibodies", J. Virol. 72: 6332-38.

Thali et al., (1993) "Characterization of Conserved Human Immunodeficiency virus Type 1 gp120 Neutralization Epitopes Exposed upon gp120-CD4 Binding", J. Virol. 67: 3978-88.

Trkola et al., (1995) "Cross-Clade Neutralization of Primary Isolates of Human Immunodeficiency Virus Type 1 by Human Monocolonal Antibodies and Tetrameric CD4-IgG", J. Virol. 69: 6609-17.

Truneh et al., (1991) "A Region in Domain 1 of CD4 Distinct from the Primary gp120 Binding Site Is Involved in HIV Infection and Virus-mediated Fusion", J. Biol. Chem. 266: 5942-48.

ISR dated Jun. 19, 2008, in the international application PCT/US05/22801.

Agwale et al., (Jul. 23, 2002) "A Tat subunit vaccine confers protective immunity against the immune-modulating activity of the human immunodeficiency virus type-1 Tat protein in mice", Proceedings of the National Academy of Sciences of USA, National Academy of Science, Washington, DC, US, vol. 99, No. 15, pp. 10037-10041, XP002226223, ISSN: 0027-8424.

Bower et al., (Oct. 25, 2004) "DNA vaccines expressing soluble CD4-envelope proteins fused to C3d elicit cross-reactive neutralizing antibodies to HIV-1," Virology, Academic Press, Orlando, vol. 328, No. 2, pp. 292-300. XP004581382, ISSN: 0042-6822.

Davio et al., (1995) Interdomain Interactions in the Chimeric Protein Toxin sCD4(178)-PE40: A Differential Scanning calorimetry (DSC) Study, Pharmaceutical Research, vol. 12, No. 5, pp. 642-648, XP008024188.

Leong et al., (1990) "Identification of the integrin binding domain of the *Yersinia psudotuberculosis* invasion protein," The EMBO Journal, vol. 9, No. 6, pp. 1979-1989, XP008119834.
Linhart et al., (Aug. 4, 2004) "Vaccine engineering improved by hybrid technology," International Archives of Allergy and Immunology, vol. 134, No. 4, pp. 324-331, XP009072133, ISSN: 1018-2438.
Wang et al., (Nov. 22, 2002) "Synthetic AIDS vaccine by targeting HIV receptor," Vaccine, Butterworth Scientific, Guildford, GB, vol. 21, No. 1-2, pp. 89-97, XP004393289, ISSN: 0264-410X.

* cited by examiner

FIGURE 1A (SEQ ID NO:1)

KKVVLGKKGDTVELTCTASQKKSIQFHWKNSNQIKILGNQGSFLTKGPSKLNDRADSRRSLWDQ
GNFPLIIKNLKIEDSDTYICEVEDQKEEVQLLVFGLTANSDTHLLQGQSLTLTLESPPGSSPSV
QCRSPRGKNIQGGKTLSVSQLELQDSGTWTCTVLQNQKKVEFKIDIVVLAFQKASSIVYKKEGE
QVEFSFPLAFTVEKLTGSGELWWQAERASSSKSWITFDLKNKEVSVKRVTQDPKLQMGKKLPLH
LTLPQALPQYAGSGNLTLALEAKTGKLHQEVNLVVMRATQLQKNLTCEVWGPTSPKLMLSLKLE
NKEAKVSKREKAVWVLNPEAGMWQCLLSDSGQVLLESNIKVLPTWSTPVQPMALIVLGGVAGLL
LFIGLGIFFCVRCRHRRRQAERMSQIKRLLSEKKTCQCPHRFQKTCSPI

FIGURE 1B (SEQ ID NO:4)

TCTASQKKSIQFHWKNSNQIKILGNQGSFLTKGPSKLNDRADSRRSLWDQGNFPLIIKNLKIED
SDTYICE

FIGURE 2A (SEQ ID NO:2)

MMVFQPISEFLLIRNAGMSMYFNKIISFNIISRIVICIFLICGMFMAGASEKYDANAPQQVQPY
SVSSSAFENLHPNNEMESSINPFSASDTERNAAIIDRANKEQETEAVNKMISTGARLAASGRAS
DVAHSMVGDAVNQEIKQWLNRFGTAQVNLNFDKNFSLKESSLDWLAPWYDSASFLFFSQLGIRN
KDSRNTLNLGVGIRTLENGWLYGLNTFYDNDLTGHNHRIGLGAEAWTDYLQLAANGYFRLNGWH
SSRDFSDYKERPATGGDLRANAYLPALPQLGGKLMYEQYTGERVALFGKDNLQRNPYAVTAGIN
YTPVPLLTVGVDQRMGKSSKHETQWNLQMNYRLGESFQSQLSPSAVAGTRLLAESRYNLVDRNN
NIVLEYQKQQVVKLTLSPATISGLPGQVYQVNAQVQGASAVREIVWSDAELIAAGGTLTPLSTT
QFNLVLPPYKRTAQVSRVTDDLTANFYSLSALAVDHQGNRSNSFTLSVTVQQPQLTLTAAVIGD
GAPANGKTAITVEFTVADFEGKPLAGQEVVITTNNGALPNKITEKTDANGVARIALTNTTDGVT
VVTAEVEGQRQSVDTHFVKGTIAADKSTLAAVPTSIIADGLMASTITLELKDTYGDPQAGANVA
FDTTLGNMGVITDHNDGTYSAPLTSTTLGVATVTVKVDGAAFSVPSVTVNFTADPIPDAGRSSF
TVSTPDILADGTMSSTLSFVPVDKNGHFISGMQGLSFTQNGVPVSISPITEQPDSYTATVVGNS
VGDVTITPQVDTLILSTLQKKISLFPVPTLTGILVNGQNFATDKGFPKTIFKNATFQLQMDNDV
ANNTQYEWSSSFTPNVSVNDQGQVTITYQTYSEVAVTAKSKKFPSYSVSYRFYPNRWIYDGGRS
LVSSLEASRQCQGSDMSAVLESSRATNGTRAPDGTLWGEWGSLTAYSSDWQSGEYWVKKTSTDF
ETMNMDTGALQPGPAYLAFPLCALSI

FIGURE 2B (SEQ ID NO:5):

QGLSFTQNGVPVSIS

FIGURE 2C (SEQ ID NO:6):

GQRQSVDTHFVK

FIGURE 2D (SEQ ID NO:7):

LTLTAAVIGDGAPANGKTAITVEFTVADFEGKPLAGQEVVITTNNGALPNKITEKTDANGVARI
ALTNTTDGVTVVTAEVEGQRQSVDTHFVK

FIGURE 2E (SEQ ID NO:8):

GTIAADKSTLAAVPTSIIADGLMASTITLELKDTYGDPQAGANVAFDTTLGNMGVITDHNDGTY
SAPLTSTTLGVATVTVKVDGAAFSVPSVTVNFTAD

FIGURE 2F (SEQ ID NO:9):

PIPDAGRSSFTVSTPDILADGTMSSTLSFVPVDKNGHFISGMQGLSFTQNGVPVSISPITEQPD
SYTATVVGNSVGDVTITPQVDTLILSTLQKKISLFPV

FIGURE 2G (SEQ ID NO:10):

PTLTGILVNGQNFATDKGFPKTIFKNATFQLQMDNDVANNTQYEWSSSFTPNVSVNDQGQVTIT
YQTYSEVAVTAKSKKFPSYSVSYRFYPNR

FIGURE 2H (SEQ ID NO:11):

LTLTAAVIGDGAPANGKTAITVEFTVADFEGKPLAGQEVVITTNNGALPNKITEKTDANGVARI
ALTNTTDGVTVVTAEVEGQRQSVDTHFVKGTIAADKSTLAAVPTSIIADGLMASTITLELKDTY
GDPQAGANVAFDTTLGNMGVITDHNDGTYSAPLTSTTLGVATVTVKVDGAAFSVPSVTVNFTAD

FIGURE 2I (SEQ ID NO:12):

LTLTAAVIGDGAPANGKTAITVEFTVADFEGKPLAGQEVVITTNNGALPNKITEKTDANGVARI
ALTNTTDGVTVVTAEVEGQRQSVDTHFVKGTIAADKSTLAAVPTSIIADGLMASTITLELKDTY
GDPQAGANVAFDTTLGNMGVITDHNDGTYSAPLTSTTLGVATVTVKVDGAAFSVPSVTVNFTAD
PIPDAGRSSFTVSTPDILADGTMSSTLSFVPVDKNGHFISGMQGLSFTQNGVPVSISPITEQPD
SYTATVVGNSVGDVTITPQVDTLILSTLQKKISLFPV

FIGURE 2J (SEQ ID NO:13):

LTLTAAVIGDGAPANGKTAITVEFTVADFEGKPLAGQEVVITTNNGALPNKITEKTDANGVARI
ALTNTTDGVTVVTAEVEGQRQSVDTHFVKGTIAADKSTLAAVPTSIIADGLMASTITLELKDTY
GDPQAGANVAFDTTLGNMGVITDHNDGTYSAPLTSTTLGVATVTVKVDGAAFSVPSVTVNFTAD
PIPDAGRSSFTVSTPDILADGTMSSTLSFVPVDKNGHFISGMQGLSFTQNGVPVSISPITEQPD
SYTATVVGNSVGDVTITPQVDTLILSTLQKKISLFPVPTLTGILVNGQNFATDKGFPKTIFKNA
TFQLQMDNDVANNTQYEWSSSFTPNVSVNDQGQVTITYQTYSEVAVTAKSKKFPSYSVSYRFYP
NR

FIGURE 3 (SEQ ID NO:3)

```
ATGATGGTTTTCCAGCCAATCAGTGAGTTTCTCTTGATAAGGAATGCGGGAATGTCTATGTATT
TTAATAAAATAATTTCATTTAATATTATTTCACGAATAGTTATTTGTATCTTTTTGATATGTGG
AATGTTCATGGCTGGGGCTTCAGAAAAATATGATGCTAACGCACCGCAACAGGTCCAGCCTTAT
TCTGTCTCTTCATCTGCATTTGAAAATCTCCATCCTAATAATGAAATGGAGAGTTCAATCAATC
CCTTTTCCGCATCGGATACAGAAAGAAATGCTGCAATAATAGATCGCGCCAATAAGGAGCAGGA
GACTGAAGCGGTGAATAAGATGATAAGCACCGGGGCCAGGTTAGCTGCATCAGGCAGGGCATCT
GATGTTGCTCACTCAATGGTGGGCGATGCGGTTAATCAAGAAATCAAACAGTGGTTAAATCGAT
TCGGTACGGCTCAAGTTAATCTGAATTTTGACAAAAATTTTTCGCTAAAAGAAAGCTCTCTTGA
TTGGCTGGCTCCTTGGTATGACTCTGCTTCATTCCTCTTTTTTAGTCAGTTAGGTATTCGCAAT
AAAGACAGCCGCAACACACTTAACCTTGGCGTCGGGATACGTACATTGGAGAACGGTTGGCTGT
ACGGACTTAATACTTTTTATGATAATGATTTGACCGGCCACAACCACCGTATCGGTCTTGGTGC
CGAGGCCTGGACCGATTATTTACAGTTGGCTGCCAATGGGTATTTTCGCCTCAATGGATGGCAC
TCGTCGCGTGATTTCTCCGACTATAAAGAGCGCCCAGCCACTGGGGGGGATTTGCGCGCGAATG
CTTATTTACCTGCACTCCCACAACTGGGGGGGAAGTTGATGTATGAGCAATACACCGGTGAGCG
TGTTGCTTTATTTGGTAAAGATAATCTGCAACGCAACCCTTATGCCGTGACTGCCGGGATCAAT
TACACCCCCGTGCCTCTACTCACTGTCGGGGTAGATCAGCGTATGGGGAAAAGCAGTAAGCATG
AAACACAGTGGAACCTCCAAATGAACTATCGCCTGGGCGAGAGTTTTCAGTCGCAACTTAGCCC
TTCAGCGGTGGCAGGAACACGTCTACTGGCGGAGAGCCGCTATAACCTTGTCGATCGTAACAAT
AATATCGTGTTGGAGTATCAGAAACAGCAGGTGGTTAAACTGACATTATCGCCAGCAACTATCT
CCGGCCTGCCGGGTCAGGTTTATCAGGTGAACGCACAAGTACAAGGGGCATCTGCTGTAAGGGA
AATTGTCTGGAGTGATGCCGAACTGATTGCCGCTGGCGGCACATTAACACCACTGAGTACCACA
CAATTCAACTTGGTTTTACCGCCTTATAAACGCACAGCACAAGTGAGTCGGGTAACGGACGACC
TGACAGCCAACTTTTATTCGCTTAGTGCGCTCGCGGTTGATCACCAAGGAAACCGATCTAACTC
ATTCACATTGAGCGTCACCGTTCAGCAGCCTCAGTTGACATTAACGGCGGCCGTCATTGGTGAT
GGCGCACCGGCTAATGGGAAAACTGCAATCACCGTTGAGTTCACCGTTGCTGATTTTGAGGGGA
AACCCTTAGCCGGGCAGGAGGTGGTGATAACCACCAATAATGGTGCGCTACCGAATAAAATCAC
GGAAAAGACAGATGCAAATGGCGTCGCGCGCATTGCATTAACCAATACGACAGATGGCGTGACG
GTAGTCACAGCAGAAGTGGAGGGGCAACGGCAAAGTGTTGATACCCACTTTGTTAAGGGTACTA
TCGCGGCGGATAAATCCACTCTGGCTGCGGTACCGACATCTATCATCGCTGATGGTCTAATGGC
TTCAACCATCACGTTGGAGTTGAAGGATACCTATGGGACCCGCAGGCTGGCGCGAATGTGGCT
TTTGACACAACCTTAGGCAATATGGGCGTTATCACGGATCACAATGACGGCACTTATAGCGCAC
CATTGACCAGTACCACGTTGGGGGTAGCAACAGTAACGGTGAAAGTGGATGGGGCTGCGTTCAG
TGTGCCGAGTGTGACGGTTAATTTCACGGCAGATCCTATTCCAGATGCTGGCCGCTCCAGTTTC
ACCGTCTCCACACCGGATATCTTGGCTGATGGCACGATGAGTTCCACATTATCCTTTGTCCCTG
TCGATAAGAATGGCCATTTTATCAGTGGGATGCAGGGCTTGAGTTTTACTCAAAACGGTGTGCC
GGTGAGTATTAGCCCCATTACCGAGCAGCCAGATAGCTATACCGCGACGGTGGTTGGGAATAGT
GTCGGTGATGTCACAATCACGCCGCAGGTTGATACCCTGATACTGAGTACATTGCAGAAAAAAA
TATCCCTATTCCCGGTACCTACGCTGACCGGTATTCTGGTTAACGGGCAAAATTTCGCTACGGA
TAAAGGGGTTCCCGAAAACGATCTTTAAAAACGCCACATTCCAGTTACAGATGGATAACGATGTT
GCTAATAATACTCAGTATGAGTGGTCGTCGTCATTCACACCCAATGTATCGGTTAACGATCAGG
GTCAGGTGACGATTACCTACCAAACCTATAGCGAAGTGGCTGTGACGGCGAAAAGTAAAAAATT
CCCAAGTTATTCGGTGAGTTATCGGTTCTACCCAAATCGGTGGATATACGATGGCGGCAGATCG
CTGGTATCCAGTCTCGAGGCCAGCAGACAATGCCAAGGTTCAGATATGTCTGCGGTTCTTGAAT
CCTCACGTGCAACCAACGGAACGCGTGCGCCTGACGGGACATTGTGGGCGAGTGGGGAGCTT
GACCGCGTATAGTTCTGATTGGCAATCTGGTGAATATTGGGTCAAAAAGACCAGCACGGATTTT
GAAACCATGAATATGGACACAGGCGCACTGCAACCAGGGCCTGCATACTTGGCGTTCCCGCTCT
GTGCGCTGTCAATATAA
```

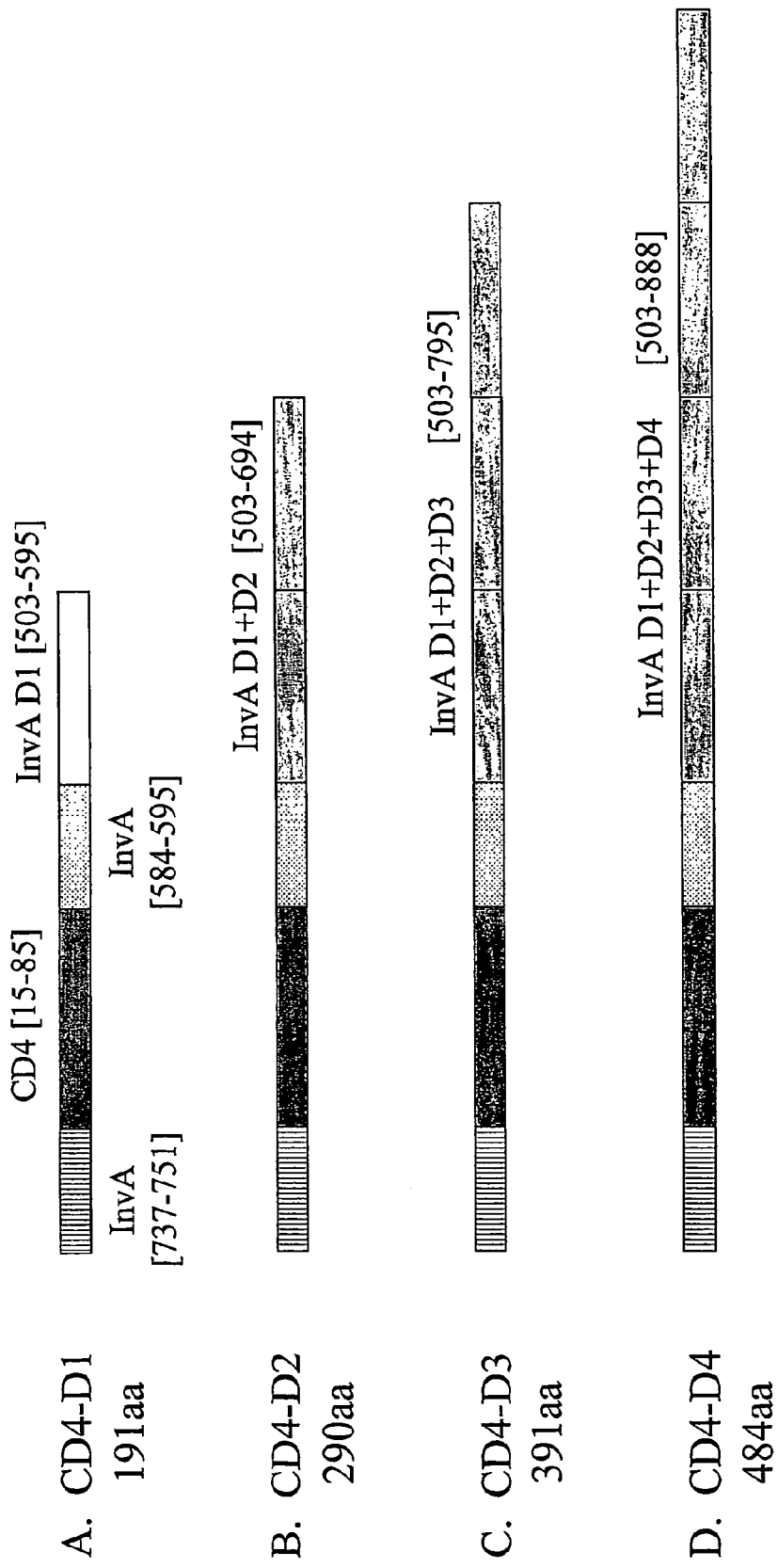
FIG. 8: Invasin-CD4 Constructs

FUSION PROTEINS COMPRISING CD4 MINIMAL MODULES AND INVASIN POLYPEPTIDES THAT ARE CAPABLE OF BINDING TO THE HIV ENVELOPE AND EXPOSING CRYPTIC NEUTRALIZIATION EPITOPES

RELATED APPLICATIONS

This application is the U.S. National Phase of International Application of International Application No. PCT/US2005/022801, filed Jun. 8, 2005 and published in English, which claims the benefit of U.S. Provisional Application No. 60/578,151, filed Jun. 8, 2004, and U.S. Provisional Application No. 60/578,211, filed Jun. 8, 2004. The above applications are incorporated herein in their entirety by reference. The above applications are incorporated herein in their entirety by reference.

STATEMENT OF GOVERNMENT SUPPORT

The application was made with support from the United States NIAID NIH HIVRAD under Grant No. 5P01 AI48225-03. Thus, the U.S. Government may have certain rights in this invention.

TECHNICAL FIELD

The invention relates generally to proteins comprising at least a portion of the Env-binding region of human CD4. The proteins described herein bind to HIV Env proteins (such as monomeric or oligomeric gp120, gp140 or gp160) and induce a conformational change in the Env protein such that conserved, cryptic epitopes participating in Env-CD4 and chemokine receptor binding are exposed. The invention also pertains to methods of using these molecules to elicit an immune response against a broad range of HIV subtypes.

BACKGROUND

The human immunodeficiency virus (HIV-1, also referred to as HTLV-III, LAV or HTLV-III/LAV) is the etiological agent of the acquired immune deficiency syndrome (AIDS) and related disorders. (see, e.g., Barre-Sinoussi, et al., (1983) *Science* 220:868-871; Gallo et al. (1984) *Science* 224:500-503; Levy et al., (1984) *Science* 225:840-842; Siegal et al., (1981) *N. Engl. J. Med.* 305:1439-1444; Guyader et al., (1987) *Nature* 326:662-669).

The envelope protein of HIV-1, HIV-2 and SIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells. Furthermore, upon binding to its receptor, CD4, the Env polypeptide undergoes a significant structural rearrangement. After this conformational change the CCR5 co-receptor binding site is exposed. Exposure of the CCR5 binding site, in turn, mediates viral entry into the host cell. See, e.g., Wyatt, R., et al. (1998) *Nature* 393:705-711; Kwong, P., et al. (1998) *Nature* 393:648-659. Env appears to be the primary target for inducing a humoral immune response to HIV.

However, it is known that antibodies directed against gp120 do not generally exhibit broad antibody responses against different HIV strains and do not induce production of neutralizing antibodies. See, e.g., Javaherian, K., et al. (1989) *Proc. Natl. Acad. Sci.* 86:6786-6772; Matsushita, M., et al. (1988) *J. Virol.* 62:2107-2144; Putney, S., et al. (1986) *Science* 234:1392-1395; Rushe, J. R., et al. (1988) *Proc. Nat. Acad. Sci. USA* 85: 3198-3202; Matthews, T. (1986) *Proc. Natl. Acad. Sci. USA.* 83:9709-9713; Nara, P. L., et al. (1988) *J. Virol.* 62:2622-2628; Palker, T. J., et al. (1988) *Proc. Natl. Acad. Sci. USA.* 85:1932-1936).

Furthermore, although neutralizing antibodies are typically generated in the course of HIV infection in humans, these antibodies do not provide permanent antiviral effect may in part be due to the generation of "neutralization escapes" virus mutants and to the general decline in the host immune system associated with pathogenesis. See, e.g., Barre-Sinoussi, F., et al. (1983) *Science* 220:868-871; Robert-Guroff, M., et al. (1985) *Nature* (London) 316:72-74; Weis, R., et al. (1985) *Nature* (London) 316:69-72; Weis, R., et al. (1986) *Nature* (London) 324:572-575. Nonetheless, it is widely believed that the presence of preexisting neutralizing antibodies upon initial HIV-1 exposure will likely have a protective effect, for instance by attaching to the incoming virions and reducing or preventing their infectivity for target cells and prevent the cell-to-cell spread of virus in tissue culture. See, e.g., Hu et al. (1992) *Science* 255:456-459; Burton, D., R. and Montefiori, D. (1997) *AIDS* 11(suppl. A): 587-598; Montefiori and Evans (1999) *AIDS Res. Hum. Ret.* 15(8):689-698; Bolognesi, D. P., et al. (1994) *Ann. Int. Med.* 8:603-611; Haynes, B., F., et al. (1996) *Science;* 271: 324-328.

Several categories of potentially effective neutralizing antibodies have been identified. For example, in most infected individuals, a subset of broadly reactive antibodies that interfere with binding of gp120 and CD4 have been identified. See, e.g., Kang, C.-Y., et al. (1991) *Proc. Natl. Acad. Sci. USA.* 88:6171-6175; McDougal, J. S., et al. (1986) *J. Immunol.* 137:2937-2944. Monoclonal antibodies, such as IgG1b12, 2G12 (Mo et al. (1997) *J. Virol* 71:6869-6874), PA14 (Trkola et al. (2001) *J. Virol.* 75(2):579-88) and 2F5 also exhibit neutralizing effects. See, also, Trkola et al. (1995) *J. Virol.* 69:6609-6617; D'Sousa et al (1997) *J. Infect. Dis.* 175:1062-1075. Other antibodies are believed to bind to the chemokine receptor-binding region after CD4 has bound to Env. See, e.g., Thali et al. (1993) *J. Virol.* 67:3978-3988). Furthermore, in order to generate antibodies against the CD4 binding site region, which is exposed only upon binding to CD4, several groups have attempted to generate neutralizing antibodies by administering complexes of Env bound to CD4 (e.g., soluble CD4, referred to as "sCD4") or to CD4 mimetics (e.g., CD4M33). See, e.g., Martin et al. (2003) *Nat. Biotechnol.* 21(1):71-76.

In addition, WO 04/037847 describes Env-CD4 complexes useful in generating immune responses. Env-CD4 (sCD4) complexes are capable of inducing broadly neutralizing antibodies presumably by targeting conformational epitopes exposed in Env protein upon binding to CD4. However, if sCD4 administered with an adjuvant, the potential for an autoimmune response is of serious concern. In addition, WO 04/037847 describes hybrid Env-CD4 polypeptides.

Despite the above approaches, there remains a need for additional molecules that can elicit an immunological response (e.g., neutralizing and/or protective antibodies) in a subject against multiple HIV strains and subtypes, for example when administered as a vaccine. The present invention solves these and other problems by providing modified Env polypeptides (e.g., gp120) complexed to novel, fusion proteins comprising CD4 mini-proteins or mimics (mimetics) in order to expose epitopes in or near the CD4 binding site.

SUMMARY

The present invention solves these and other problems by providing fusion proteins comprising a CD4 Env-binding region (CD4 minimal module) in a non-CD4 scaffold (backbone). The overall structure of the fusion protein mimics the conformation of native CD4, thus presenting the CD4 minimal module in a form that is known to bind to Env. Binding of CD4 to Env induces a conformational change in Env that appears to expose epitopes to which neutralizing antibodies are more readily generated. Thus, by using a CD4 minimal module within a non-CD4 scaffold, the fusion molecules described herein allow for the production of useful antibodies against CD4-Env (including neutralizing antibodies and other immune responses), while reducing or eliminating unwanted immune responses to non-Env binding regions of CD4. Also provided are complexes of Env with the fusion proteins described herein, as well as antibodies directed against these fusion proteins.

Thus, in one aspect, the invention includes a fusion protein comprising a CD4 minimal module and one or more heterologous polypeptide sequences. In certain embodiments, the heterologous polypeptide sequence(s) is(are) structurally similar to one or more regions of CD4 (e.g., one or more regions of an invasin polypeptide from *Yesinia pseudotuberculosis*). The CD4 minimal module is preferably a human CD4 sequence. In certain embodiments, the fusion protein further comprises one or more additional polypeptides, for example immunomodulatory polypeptides (cytokines, etc.), and/or one or more Env polypeptides.

In another aspect, the invention includes complexes of the fusion proteins described herein and an HIV Env polypeptide. Preferably, the complexes are formed such that cryptic epitopes are exposed in the Env polypeptide. The HIV Env polypeptide and CD4 protein can be complexed by crosslinking (e.g., using formaldehyde); using a fixative (e.g., formalin); and/or can complex spontaneously under suitable conditions.

In another aspect, the invention includes a polynucleotide encoding any of the CD4 mini protein containing fusion proteins described herein. In certain embodiments, the CD4-encoding polynucleotide sequences are inserted into (or embedded) within the sequences encoding the heterologous (e.g., Invasin) polypeptides, for example such that the overall configuration of the fusion protein is similar to that of native CD4. Optionally, additional sequences can be included in the fusion proteins described herein. Further, when any of the polynucleotides described herein are expressed, the fusion protein preferably complexes with an HIV Env polypeptide such that cryptic epitopes are exposed in the Env polypeptide.

In yet another aspect, the invention includes immunogenic compositions comprising any of the polynucleotides and/or polypeptides described herein. In certain embodiments, the immunogenic compositions further comprise one or more adjuvants.

In a still further aspect, the invention includes a cell comprising any of the polynucleotides and/or polypeptides described herein. The polynucleotide sequences are preferably operably linked to control elements compatible with expression in the selected cell. The cell can be, for example, a mammalian cell. (e.g., PERC.6, BHK, VERO, HT1080, 293, RD, COS-7, and CHO cells); an avian cell (e.g., EBx® cells); an insect cell (e.g., *Trichoplusia ni* (Tn5) or Sf9 cells); a bacterial cell; a yeast cell; a plant cell; an antigen presenting cell; a lymphoid cell selected from the group consisting of macrophage, monocytes, dendritic cells, B-cells, T-cells, stem cells, and progenitor cells thereof; a primary cell; an immortalized cell; and/or a tumor-derived cell.

In another aspects, the invention includes a gene delivery vector for use in a mammalian subject, comprising a suitable gene delivery vector for use in said subject, wherein the vector comprises any of the polynucleotides described herein operably linked to control elements compatible with expression in the subject.

In yet another aspect, the invention includes a method of producing antibodies that bind to cryptic epitopes of HIV Env, the methods comprising the step of administering any of the polypeptides described herein to a subject under conditions that allow production of antibodies (e.g., neutralizing antibodies, monoclonal antibodies, polyclonal antibodies) in the subject. In certain embodiments, the antibodies produced in the subject are then isolated.

In a still further aspect, the invention includes a method for producing any of the fusion proteins described herein, said method comprising incubating any of the cells described herein, under conditions suitable for producing said fusion protein.

In a still further aspect, the invention includes a method for producing complexes of any of the fusion proteins described herein with HIV Env, the method comprising incubating a fusion protein as described herein (or polynucleotide encoding said fusion protein) under conditions suitable for producing a complex of the fusion protein with HIV Env.

In yet another aspect, the invention includes a method of inducing an immune response (e.g., a humoral response such as a neutralizing antibody response and/or a cellular immune response) in subject comprising, administering any of the polynucleotides, polypeptides and/or immunogenic compositions described herein to a subject in an amount sufficient to induce an immune response in the subject. In certain embodiments, the method comprises transfecting cells ex vivo and reintroducing the transfected cells into the subject. In other embodiments, the method includes DNA immunization of a subject, for example, by introducing any of the polynucleotides and/or gene delivery vectors described herein into said subject under conditions that are compatible with expression of said expression cassette and production of a polypeptide in said subject. In other embodiments, the methods comprise (a) administering a first composition comprising any of the polynucleotides described herein in a priming step and (b) administering a second composition comprising any of the polypeptides described herein, as a booster, in an amount sufficient to induce an immune response in the subject. In any of the methods described herein, the vectors may comprise non-viral vectors or viral vectors. Exemplary viral vectors include, but are not limited to alphaviral vectors, retroviral vectors, and lentiviral vectors. Further, the polynucleotides and/or vector may be introduced, for example, using a particulate carrier (e.g., coated on a gold or tungsten particle and said coated particle is delivered to said subject using a gene gun) or encapsulated in a liposome preparation. In any of the methods described herein, the subject can be a mammal, for example a human or non-human mammal and the introduction can be intramuscularly, intramucosally, intranasally, subcutaneously, intradermally, transdermally, intravaginally, intrarectally, orally and/or intravenously.

The following embodiments are encompassed by the present invention:

1. A fusion protein comprising a CD4 minimal module that binds to HIV Env and one or more heterologous polypeptide sequences, wherein the tertiary structure of the fusion protein exhibits structural similarity to native CD4.

2. The fusion protein of embodiment 1, wherein the CD4 minimal module comprises residues 15 to 85 of CD4.

3. The fusion protein of embodiment 1 or embodiment 2, wherein one or more of the heterologous polypeptides are obtained from *Yersinia tuberculosis* invasin.

4. The fusion protein of embodiment 3, having a sequence shown in FIG. 7 or FIG. 8.

5. The fusion protein of any of the embodiment 1-3, further comprising additional heterologous.

6. The fusion protein of embodiment 5, wherein the additional heterologous polypeptides are selected from the group consisting of viral polypeptides, immunomodulatory polypeptides and bacterial 7. The fusion protein of embodiment 6, wherein the additional heterologous polypeptide is a viral polypeptide and the virus is HIV.

8. The fusion protein of embodiment 7, wherein the polypeptide is an HIV Env polypeptide.

9. The fusion protein of embodiment 8, wherein the HIV Env polypeptide comprises gp140 or gp120.

10. A polynucleotide encoding the fusion protein of any of embodiment 1-9.

11. A polypeptide complex comprising an HIV Env polypeptide complexed to the fusion protein of any of embodiment 1-9.

12. The polypeptide of embodiment 11, wherein the Env polypeptide and CD4protein are complexed using a fixative or via cross-linking.

13. The polypeptide of embodiment 12, wherein the fixative comprises formalin.

14. The polypeptide of embodiment 12, wherein the fixative comprises formalin.

15. The polypeptide of embodiment 11, wherein the Env polypeptide and CD4 protein complex spontaneously.

16. The polypeptide of embodiment 11, wherein the Env polypeptide comprises oligomeric gp140.

17. The polypeptide of embodiment 11, wherein the Env polypeptide comprises gp120.

18. The polypeptide of embodiment 11, wherein the fusion protein is shown in FIG. 7.

19. The polypeptide of embodiment 11, wherein the Env polypeptide and the fusion protein are cross-linked using formaldehyde.

20. An immunogenic composition comprising a fusion protein according to embodiment 1-9.

21. An immunogenic composition comprising a polypeptide complex according to embodiment 11-19.

22. The immunogenic composition according to embodiment 20 or 21, further comprising an adjuvant.

23. A cell comprising the polynucleotide of embodiment 10, and wherein said polynucleotide sequence is operably linked to control elements compatible with expression in the selected cell.

24. The cell of embodiment 23, wherein the cell is a mammalian cell.

25. The cell of embodiment 23, wherein the cell is selected from the group consisting of BHK, VERO, HT1080, 293, RD, COS-7, and CHO cells.

26. The cell of embodiment 25, wherein said cell is a CHO cell.

27. The cell of embodiment 23, wherein the cell is an insect cell.

28. The cell of embodiment 27, wherein the cell is either *Trichoplusia ni* (Tn5) or Sf9 insect cells.

29. The cell of embodiment 23, wherein the cell is a bacterial cell.

30. The cell of embodiment 23, wherein the cell is a yeast cell.

31. The cell of embodiment 23, wherein the cell is a plant cell.

32. The cell of embodiment 23, wherein the cell is an antigen presenting cell.

33. The cell of embodiment 23, wherein the cell is a lymphoid cell selected from the group consisting of macrophage, monocytes, dendritic cells, B-cells, T-cells, stem cells, and progenitor cells thereof.

34. The cell of embodiment 23, wherein the cell is a primary cell.

35. The cell of embodiment 23, wherein the cell is an immortalized cell.

36. The cell of embodiment 23, wherein the cell is a tumor-derived cell.

37. A gene delivery vector for use in a mammalian subject, comprising a suitable gene delivery vector for use in said subject, wherein the vector comprises a polynucleotide according to embodiment 10, and wherein said polynucleotide sequence is operably linked to control elements compatible with expression in the subject.

38. A method of producing antibodies that bind to cryptic epitopes of HIV Env, the methods comprising the step of:
administering a polypeptide according to embodiments 21 or 22 to a subject under conditions that allow production of antibodies in the subject.

39. The method of embodiment 38, further comprising the step of isolating the antibodies produced in the subject.

40. The method of embodiment 38 or 39, wherein the antibodies are neutralizing antibodies.

41. The method of embodiment 38-40, wherein the antibodies are monoclonal antibodies.

42. The method of embodiment 38-40, wherein the antibodies are polyclonal antibodies.

43. A method for producing a polypeptide including HIV Env polypeptide sequences complexed to CD4 proteins, said method comprising, incubating the cells of embodiments 23-36, under conditions for producing said polypeptide.

44. A method of inducing an immune response in subject comprising, administering composition according to embodiment 20-22 in an amount sufficient to induce an immune response in the subject.

45. A method of DNA immunization of a subject, comprising, introducing a gene delivery vector of embodiment 37 into said subject under conditions that are compatible with expression of said expression cassette in said subject.

46. The method of embodiment 45, wherein said gene delivery vector is a nonviral vector.

47. The method of embodiment 45, wherein said vector is delivered using a particulate carrier.

48. The method of embodiment 47, wherein said vector is coated on a gold or tungsten particle and said coated particle is delivered to said subject using a gene gun.

49. The method of embodiment 45, wherein said vector is encapsulated in a liposome preparation.

50. The method of embodiment 45, wherein said vector is a viral vector.

51. The method of embodiment 50, wherein said viral vector is a retroviral vector.

52. The method of embodiment 50, wherein said viral vector is a lentiviral vector.

53. The method of embodiment 45, wherein said subject is a mammal.

54. The method of embodiment 53, wherein said mammal is a human.

55. A method of generating an immune response in a subject, comprising transfecting cells of said subject a gene delivery vector of embodiment 45, under conditions that permit the expression of said polynucleotide and production of said polypeptide, thereby eliciting an immunological response to said polypeptide.

56. The method of embodiment 55, wherein said vector is a nonviral vector.

57. The method of embodiment 56, wherein said vector is delivered using a particulate carrier.

58. The method of embodiment 57, wherein said vector is coated on a gold or tungsten particle and said coated particle is delivered to said vertebrate cell using a gene gun.

59. The method of embodiment 57, wherein said vector is encapsulated in a liposome preparation.

60. The method of embodiment 55, wherein said vector is a viral vector.

61. The method of embodiment 55, wherein said viral vector is a retroviral vector.

62. The method of embodiment 61, wherein said viral vector is a lentiviral vector.

63. The method of embodiment 55, wherein said subject is a mammal.

64. The method of embodiment 63, wherein said mammal is a human.

65. The method of embodiment 55, wherein said transfecting is done ex vivo and said transfected cells are reintroduced into said subject.

66. The method of embodiment 55, wherein said transfecting is done in vivo in said subject.

67. The method of embodiment 55, where said immune response is a humoral immune response.

68. The method of embodiment 55, where said immune response is a cellular immune response.

69. The method of embodiment 55-68, wherein the gene delivery vector is administered intramuscularly, intramucosally, intranasally, subcutaneously, intradermally, transdermally, intravaginally, intrarectally, orally or intravenously.

70. A method of inducing an immune response in a subject comprising (a) administering a first composition comprising a polynucleotide according to embodiment 10 in a priming step and (b) administering a second composition comprising a polypeptide according to embodiments 1-9, as a booster, in an amount sufficient to induce an immune response in the subject.

71. The method of embodiment 70, wherein the first composition or second composition further comprise an adjuvant.

72. The method of embodiment 70, wherein the first composition further comprises a sequence encoding an HIV Gag polypeptide.

73. The method of embodiment 70, wherein the second composition further comprises an HIV Gag polypeptide.

These and other embodiments of the subject invention will readily occur to those of skill in the art in light of the disclosure herein.

BRIEF DESCRIPTION OF THE DRAWINGS

FIG. 1A (SEQ ID NO:1) depicts the primary amino acid sequence of a human CD4 protein (GenBank Accession No. NP_000607).

FIG. 1B (SEQ ID NO:4) depicts the primary amino acid sequence of a human CD minimal module.

FIG. 2A (SEQ ID NO:2) depicts the primary amino acid sequence of an invasin protein from *Yersinia tuberculosis* (GenBank Accession Nos. AAA27632 and A29646).

FIG. 2B (SEQ ID NO:5) depicts the primary amino acid sequence of a fragment (residues 737-751) of the invasin protein shown in FIG. 2A.

FIG. 2C (SEQ ID NO:6) depicts the primary amino acid sequence of a fragment (residues 584-595) of the invasin protein shown in FIG. 2A.

FIG. 2D (SEQ ID NO:7) depicts the primary amino acid sequence of a fragment (residues 503-595) of the invasin protein shown in FIG. 2A. SEQ ID NO:7 is also referred to as Domain 1 (D1) of invasin.

FIG. 2E (SEQ ID NO:8) depicts the primary amino acid sequence of a fragment (residues 596-694) of the invasin protein shown in FIG. 2A. SEQ ID NO:8 is also referred to as Domain 2 (D2) of invasin.

FIG. 2F (SEQ ID NO:9) depicts the primary amino acid sequence of a fragment (residues 695-795) of the invasin protein shown in FIG. 2A. SEQ ID NO:9 is also referred to as Domain 3 (D3) of invasin.

FIG. 2G (SEQ ID NO:10) depicts the primary amino acid sequence of a fragment (residues 796-888) of the invasin protein shown in FIG. 2A. SEQ ID NO:10 is also referred to as Domain 4 (D4) of invasin.

FIG. 2H (SEQ ID NO:11) depicts the primary amino acid sequence of a fragment (residues 503-694) of the invasin protein shown in FIG. 2A. SEQ ID NO:11 includes D1 (SEQ ID NO:7) and D2 (SEQ ID NO:8).

FIG. 2I (SEQ ID NO:12) depicts the primary amino acid sequence of a fragment (residues 503-795) of the invasin protein shown in FIG. 2A. SEQ ID NO:12 includes D1 (SEQ ID NO:7); D2 (SEQ ID NO:8) and D3 (SEQ ID NO:9).

FIG. 2J (SEQ ID NO:13) depicts the primary amino acid sequence of a fragment (residues 503-888) of the invasin protein shown in FIG. 2A. SEQ ID NO:13 includes D1 (SEQ ID NO:7); D2 (SEQ ID NO:8); D3 (SEQ ID NO:9) and D4 (SEQ ID NO:10).

FIG. 3 (SEQ ID NO:3) depicts an invasin-encoding polynucleotide (GenBank Accession No. M17448).

FIG. 4 is a schematic diagram depicting a CD4 mini-protein involved in gp120 binding. The CD4 minimal module (darker gray) corresponds to residues 15-85 of SEQ ID NO:1 and is structurally stabilized by the presence of a disulfide bridge between Cys16 and Cys84.

FIG. 5 is a schematic diagram comparing tertiary structure of CD4 (top) with invasin (bottom). A CD4 minimal module is shown in darker gray.

FIG. 6, panels A and B, are schematics depicting structural similarity between various regions of CD4 and invasin. Panel A shows structural similarity between residues 1-14 of CD4 (right) and residues 737-751 of invasin (left). Panel B shows structural similarity between residues 78-109 of CD4 (left) and residues 576-603 of invasin (right).

FIG. 7 is schematic depiction of an exemplary fusion protein as described herein comprising a CD4 minimal module (dark gray) in a single protein with fragments of invasin.

FIG. 8, panels A-D, are schematic depictions of additional exemplary fusion proteins as described herein comprising a CD4 minimal module (dark gray) flanked by polypeptide fragments of invasin. Residues 737-751 of invasin are depicted with stripes. Residues 584-595 are shown as a stippled bar and additional invasin fragments (residues 503-888 or fragments thereof) are light gray.

DETAILED DESCRIPTION

The practice of the present invention will employ, unless otherwise indicated, conventional methods of protein chemistry, viral immunobiology, molecular biology and recombinant DNA techniques within the skill of the art. Such techniques are explained fully in the literature. See, e.g., T. E. Creighton, *Proteins: Structures and Molecular Properties* (W.H. Freeman and Company, 1993); Nelson L. M. and Jerome H. K. *HIV Protocols* in Methods in Molecular Medicine, vol. 17, 1999; Sambrook, et al., *Molecular Cloning: A Laboratory Manual* (Cold Spring Harbor Laboratory, 1989); F. M. Ausubel et al. *Current Protocols in Molecular Biology*, Greene Publishing Associates & Wiley Interscience New York; and Lipkowitz and Boyd, *Reviews in Computational Chemistry*, volumes 1-present (Wiley-VCH, New York, N.Y., 1999).

Figure 4:
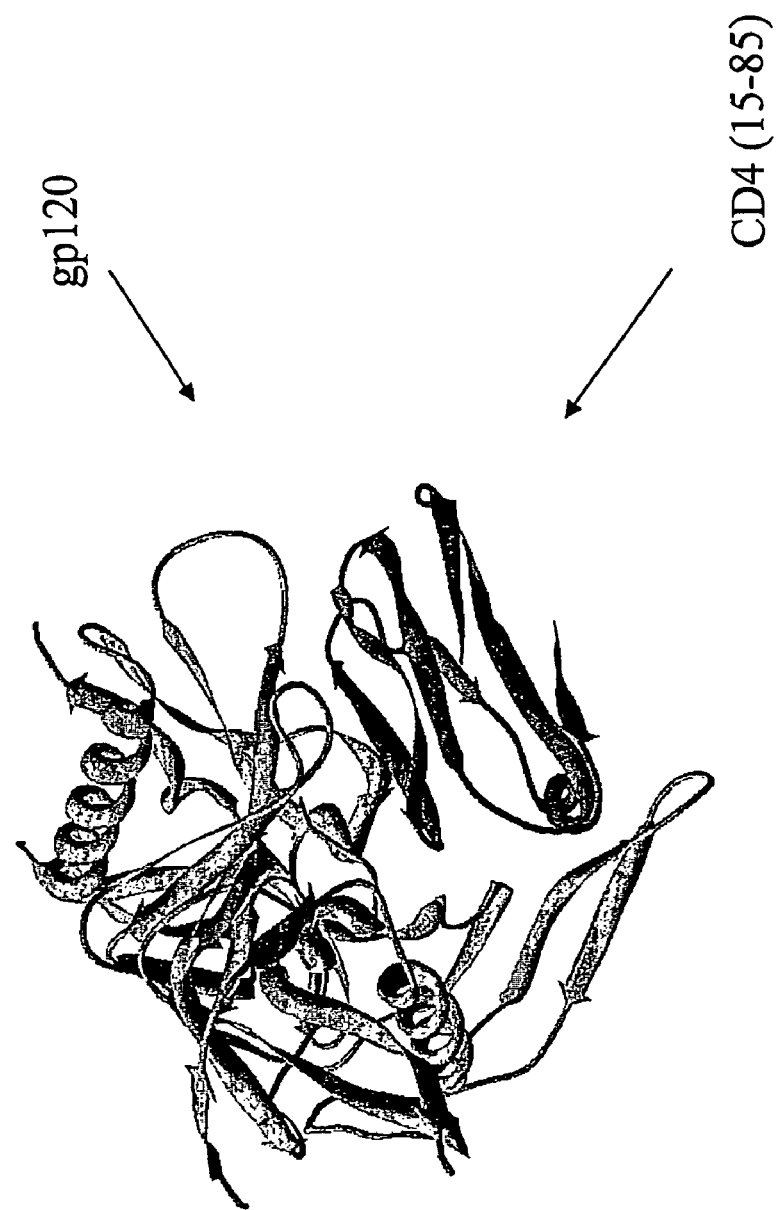

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

All publications, patents and patent applications cited herein, whether supra or infra, are hereby incorporated by reference in their entirety.

DEFINITIONS

In describing the present invention, the following terms will be employed, and are intended to be defined as indicated below.

The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include post expression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (O), Glu (E), Gly (G), H is (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl)glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents that will find use in the present invention are set forth below.

The term "peptide" also includes proteins comprising non-naturally occurring peptide-like molecules, including, but not limited to peptoids. Peptoids are an easily synthesized class of peptidomimetic oligomer that are highly diverse in structure and are stable to enzymatic and chemical degradation (Miller, S. M. et al. Proteolytic Studies of Homologous peptide and N-Substituted Glycine Peptoid Oligomers. *Bioorg. Med. Chem. Lett.* (1994), 4, 2657-2662). Hundreds of different side chains can be incorporated into the peptoid structure, including polar, reactive and even heterocyclic functionalities [Zuckermann, R. N., Kerr, J. M., Kent, S. B. H. & Moos, W. H. Efficient Method for the Preparation of Peptoids [Oligo (N-substituted glycines)] by Submonomer Solid Phase Synthesis. *J. Am. Chem. Soc.* (1992), 114, 10646-10647; Figliozzi, G. M., Goldsmith, R., Ng, S., Banville, S.C. & Zuckermann, R. N. Synthesis of N-(substituted)glycine Peptoid Libraries. *Methods Enzymol.* (1996), 267, 437-447; Burkoth, T. S., Fafarman, A. T., Charych, D. H., Connolly, M. D. & Zuckermann, R. N. Incorporation of Unprotected Heterocyclic Side Chains into Peptoid Oligomers via Solid-Phase Submonomer Synthesis. *J. Am. Chem. Soc.* (2003), 125, 8841-8845; Uno, T., Beausoleil, E., Goldsmith, R. A., Levine, B. H. & Zuckermann, R. N. New Submonomers for Poly N-Substituted Glycines (Peptoids). *Tetrahedron Lett.* (1999), 40, 1475-1478]. The ability to efficiently incorporate a wide variety of structural features allows rapid synthesis of biomimetic oligomers with far more chemical diversity than natural peptides. Thus, the peptides of the present invention (e.g., CD4 minimal modules, invasin-derived polypeptides, fusions thereof) may include one or more peptoids.

By "geometry," "architecture," or "tertiary structure" of a polypeptide or protein is meant the overall 3-D configuration of the protein. As described herein, the geometry can be determined, for example, by crystallography studies or by using various programs or algorithms that predict the geometry based on interactions between the amino acids making up the primary and secondary structures.

By "wild type" or "native" polypeptide, polypeptide agent or polypeptide drug, is meant a naturally occurring polypeptide sequence, and its corresponding secondary structure. An "isolated" or "purified" protein or polypeptide is a protein that is separate and discrete from a whole organism with which the protein is normally associated in nature. It is apparent that the term denotes proteins of various levels of purity. Typically, a composition containing a purified protein will be one in which at least about 35%, preferably at least about 40-50%, more preferably, at least about 75-85%, and most preferably at least about 90% or more, of the total protein in the composition will be the protein in question.

The terms "CD4 mini-protein," "CD4 minimal module" and "mini CD4 protein" are used interchangeably to refer to any polypeptide that interacts with env, preferably such that functional epitopes (e.g., cryptic epitopes) in or near the CD4 and/or chemokine receptor binding sites(s) are exposed. Thus, a CD mini-protein can be a less than full-length fragment of CD4, including truncations and deletions. In addition, the term encompasses functional and structural homologs of CD4 fragments, i.e., polypeptides that expose the cryptic epitopes on an Env protein. The amino acid sequence for human CD4 is incorporated herein from Maddon et al. (1985) *Cell* 42:93; and Littman et al. (1988) *Cell* 55:541) and shown as FIG. 1 (SEQ ID NO:1). In addition, the terms encompass functional and structural homologs of CD4 fragments, i.e., mimetics and/or polypeptides that expose the cryptic epitopes on an Env protein. See, e.g., Martin et al. (2003) *Nat. Biotech.* 21(1):71-76; Vita et al. (1998) *Biopolymers* 47(1):93-100; Vita et al. (1999) *Proc. Natl. Acad. Sci. USA* 96(23):13091-13096. As noted above, the CD4 proteins described herein may include one or more "peptoid" molecules, for example, peptoid mimics of CD4 binding residues such as Phe43 and Arg59 and/or peptoids that further mimic the CD4 beta-turn motif by incorporating a beta-turn inducing amino acid such as Fmoc-3-amino-1-carboxymethylcaprolactame.

By "Env polypeptide" is meant a molecule derived from an envelope protein, preferably from HIV Env. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers, dimers or multimers.

By a "gp120 polypeptide" is meant a molecule derived from a gp120 region of the Env polypeptide. Preferably, the gp120 polypeptide is derived from HIV Env. The primary amino acid sequence of gp120 is approximately 511 amino acids, with a polypeptide core of about 60,000 Daltons. The polypeptide is extensively modified by N-linked glycosylation to increase the apparent molecular weight of the molecule to 120,000 Daltons. The amino acid sequence of gp120 contains five relatively conserved domains interspersed with five hypervariable domains. The positions of the 18 cysteine residues in the gp120 primary sequence of the HIV-1$_{HXB-2}$ (hereinafter "HXB-2") strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4. A "gp120 polypeptide" includes both single subunits and/or multimers. Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 119 (Cys) to amino acid residue 123 (Thr) while β-3 occurs at approximately amino acid residue 199 (Ser) to amino acid residue 201 (Ile), relative to HXB-2. The "V1/V2 region" occurs at approximately amino acid positions 126 (Cys) to residue 196 (Cys), relative to HXB-2. (see, e.g., Wyatt et al. (1995) *J. Virol.* 69:5723-5733; Stamatatos et al. (1998) *J. Virol.* 72:7840-7845). Extruding from the second pair of β-strands (β-20 and β21) is a "small-loop" structure, also referred to herein as "the bridging sheet small loop." In HXB-2, β-20 extends from about amino acid residue 422 (Gln) to amino acid residue 426 (Met) while β-21 extends from about amino acid residue 430 (Val) to amino acid residue 435 (Tyr). In variant SF162, the Met-426 is an Arg (R) residue. The "small loop" extends from about amino acid residue 427 (Trp) through 429 (Lys), relative to HXB-2. Alignment of the amino acid sequences of Env polypeptide gp160 of any HIV variant can be determined relative to other variants, such as HXB-2, as described for example, in WO 00/39303.

Furthermore, an "Env polypeptide" or "gp120 polypeptide" as defined herein is not limited to a polypeptide having the exact sequence described herein. Indeed, the HIV genome is in a state of constant flux and contains several variable domains that exhibit relatively high degrees of variability between isolates. It is readily apparent that the terms encompass Env (e.g., gp120) polypeptides from any of the identified HIV isolates, as well as newly identified isolates, and subtypes of these isolates. Descriptions of structural features are given herein with reference to HXB-2. One of ordinary skill in the art in view of the teachings of the present disclosure and the art can determine corresponding regions in other HIV variants (e.g., isolates HIV$_{IIIb}$, HIV$_{SF2}$, HIV-1$_{SF162}$, HIV-1$_{SF170}$, HTV$_{LAV}$, HIV$_{LAI}$, HIV$_{MN}$, HIV-1$_{CM235}$, HIV-1$_{US4}$, other HIV-1 strains from diverse subtypes (e.g., subtypes, A through G, and O), HIV-2 strains and diverse subtypes (e.g., HIV-2$_{UC1}$ and HIV-2$_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the modified Env polypeptides can be based on any HIV variant.

Additionally, the term "Env polypeptide" (e.g., "gp120 polypeptide") encompasses proteins that include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

Thus, a "modified Env polypeptide" is an Env polypeptide (e.g., gp120 as defined above), which has been complexed to a fusion protein comprising a CD4 minimal module as described herein. The Env polypeptide may be monomeric or oligomeric. Generally, complexed Env (e.g., gp120) polypeptides result in exposure of epitopes in or near the CD4 binding site, while allowing correct folding (e.g., correct geometry) of the Env polypeptide. Additionally, modifications (e.g., truncations) to the V1 and V2 loop regions may also be made. Although not all possible V1/V2 modifications have been exemplified herein, it is to be understood that other disrupting modifications are also encompassed by the present invention.

The term "fusion molecule" refers to a molecule in which two or more subunit molecules are linked, typically covalently or non-covalently. The subunit molecules can be the same chemical type of molecule, or can be different chemical types of molecules. Thus, as used herein, the term refers to any molecule comprising CD4 minimal modules and at least one heterologous non-CD4 polypeptide. Fusion molecules include, but are not limited to, fusion polypeptides (for example, a fusion between a CD4 polypeptide and a non-CD4 polypeptide) and fusion nucleic acids (for example, a nucleic acid encoding the fusion polypeptide). When used in reference to proteins comprising one or more CD4 minimal modules, the terms "fusion protein" or "fusion polypeptide" refer to polypeptides in which CD4 amino acid sequences (e.g., Env-binding sequences) and one or more heterologous (non-CD4) polypeptides are expressed in a single protein. The CD4 polypeptide(s) may be flanked on one or both sides by the heterologous polypeptide(s). Non-limiting examples of heterologous (non-CD4) amino acid sequences that can be used in constructing fusion molecules with CD4 minimal modules, as described herein, include proteins or fragments or derivatives thereof having a similar tertiary structure to native CD4. For example, suitable heterologous proteins having a compatible tertiary structure include fragments of *Yersinia* tuberculosis protein invasin. A wild-type invasin amino acid sequence is shown in FIG. 2 (SEQ ID NO:2). See, also, Isberg et al. (1987) *Cell* 50(5):769-778; GenBank Accession Nos. AAA27632 and A29646. Non-limiting examples of fragments of invasin useful in constructing fusion proteins as described herein include a region extending from about amino acid residue 506 to about amino acid residue 599; a region extending from about amino acid residue 737 to about amino acid residue 751; a region extending from about amino acid residue 576 to about amino acid residue 603; and/or a region extending from about amino acid residue 584 to about amino acid residue 595. It will be apparent that one or more residues can be altered as compared to wild-type, for example, by deletion, addition or substitutions. Furthermore, one or more naturally occurring amino acid residues may be substituted with non-naturally occurring residues such as peptoids.

By "binding" is meant the ability of a fusion molecule to specifically interact with an Env polypeptide such that interaction results in a conformational change in the Env polypeptide that leads to exposure of Env epitopes to which neutralizing antibodies are more readily generated.

Normally, fusion proteins are capable of secretion into growth medium in which an organism expressing the protein is cultured. However, for purposes of the present invention, such polypeptides may also be recovered intracellularly. Secretion into growth media is readily determined using a number of detection techniques, including, e.g., polyacrylamide gel electrophoresis and the like, and immunological techniques such as Western blotting and immunoprecipitation assays as described in, e.g., International Publication No. WO 96/04301.

A polypeptide (e.g., gp120 or other Env polypeptide) is produced "intracellularly" when it is found within the cell, either associated with components of the cell, such as in association with the endoplasmic reticulum (ER) or the Golgi Apparatus, or when it is present in the soluble cellular fraction. The polypeptides of the present invention may also be secreted into growth medium so long as sufficient amounts of the polypeptides remain present within the cell such that they can be purified from cell lysates using techniques described herein.

An "immunogenic molecule" or "immunogenic composition" refers to a molecule that includes at least one epitope such that the molecule is capable of either eliciting an immunological reaction in an individual to which the protein is administered or, in the diagnostic context, is capable of reacting with antibodies directed against the HIV in question.

By "epitope" is meant a site on an antigen to which specific B cells and/or T cells respond, rendering the molecule including such an epitope capable of eliciting an immunological reaction or capable of reacting with HIV antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709-715 (technique for identifying peptides with high affinity for a given antibody). Antibodies that recognize the same epitope can be identified in a simple immunoassay showing the ability of one antibody to block the binding of another antibody to a target antigen. A "cryptic epitope" refers generally to an epitope that is exposed only in certain conformations of the protein.

A "functional epitope" refers to an epitope that elicits antibody which prevents or limits HIV infection. In a particular embodiment, the antibodies are neutralizing antibodies. In other embodiments, the antibodies can, e.g., elicit an ADCC response.

An "immunological response" or "immune response" as used herein can include the development in the subject of a humoral and/or a cellular immune response to the Env (e.g., gp120) polypeptide when the polypeptide is present in a vaccine composition. Antibodies elicited in an immune response may also neutralize infectivity, and/or mediate antibody-complement or antibody dependent cell cytotoxicity to provide protection to an immunized host. Immunological reactivity may be determined in standard immunoassays, such as a competition assays, well known in the art.

The term "antibody" as used herein includes antibodies obtained from both polyclonal and monoclonal preparations, as well as, the following: (i) hybrid (chimeric) antibody molecules (see, for example, Winter et al. (1991) *Nature* 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); (vii) human antibody molecules; and, (viii) any functional fragments obtained from such molecules, wherein such fragments retain specific-binding properties of the parent antibody molecule.

Thus, the term "antibody" refers to a polypeptide or group of polypeptides that comprise at least one antigen binding site. An "antigen binding site" is formed from the folding of the variable domains of an antibody molecule(s) to form three-dimensional binding sites with an internal surface shape and charge distribution complementary to the features of an epitope of an antigen, which allows specific binding to form an antibody-antigen complex. An antigen binding site may be formed from a heavy- and/or light-chain domain (VH and VL, respectively), which form hypervariable loops that contribute to antigen binding. The term "antibody" includes, without limitation, polyclonal antibodies, monoclonal antibodies, chimeric antibodies, altered antibodies, univalent antibodies, Fab proteins, and single-domain antibodies. In many cases, the binding phenomena of antibodies to antigens is equivalent to other ligand/anti-ligand binding.

If polyclonal antibodies are desired, a selected mammal (e.g., mouse, rabbit, goat, horse, etc.) is immunized with an immunogenic polypeptide bearing the selected epitope(s). Serum from the immunized animal is collected and treated according to known procedures. If serum containing polyclonal antibodies to an HCV epitope contains antibodies to other antigens, the polyclonal antibodies can be purified by immunoaffinity chromatography. Techniques for producing and processing polyclonal antisera are known in the art, see for example, Mayer and Walker, eds. (1987) IMMUNOCHEMICAL METHODS IN CELL AND MOLECULAR BIOLOGY (Academic Press, London).

One skilled in the art can also readily produce monoclonal antibodies directed against HCV epitopes. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980) HYBRIDOMA TECHNIQUES; Hammerling et al. (1981), MONOCLONAL ANTIBODIES AND T-CELL HYBRIDOMAS; Kennett et al. (1980) MONOCLONAL ANTIBODIES; see also, U.S. Pat. Nos. 4,341,761; 4,399,121; 4,427,783; 4,444,887; 4,466,917; 4,472,500; 4,491,632; and 4,493,890. Panels of monoclonal antibodies produced against HCV epitopes can be screened for various properties; i.e., for isotype, epitope affinity, etc. As used herein, a "single domain antibody" (dAb) is an antibody that is comprised of an HL domain, which binds specifically with a designated antigen. A dAb does not contain a VL domain, but may contain other antigen binding domains known to exist to antibodies, for example, the kappa and lambda domains. Methods for preparing dabs are known in the art. See, for example, Ward et al, Nature 341: 544 (1989).

Antibodies can also be comprised of VH and VL domains, as well as other known antigen binding domains. Examples of these types of antibodies and methods for their preparation and known in the art (see, e.g., U.S. Pat. No. 4,816,467), and include the following. For example, "vertebrate antibodies" refers to antibodies that are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids can also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region can be made to alter antigen binding characteristics. The antibody can also be engineered to aid the specific delivery of a molecule or substance to a specific cell or tissue site. The desired alterations can be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation. See, e.g., Glennie et al. Nature 295:712 (1982). Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)2), which are capable of selectively reacting with a designated antigen or antigen family. Fab antibodies can be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Antigen-antibody complex" refers to the complex formed by an antibody that is specifically bound to an epitope on an antigen.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

Generally, the polypeptides and/or polynucleotides of the present invention can or may include related sequences having about 80% to 100%, greater than about 80-85%, preferably greater than 90-92%, more preferably greater than 95%, and most preferably greater than 98% sequence (including all integer values falling within these described ranges) identity to the molecules described herein (for example, to the claimed sequences or other sequences of the present invention) when the sequences of the present invention are used as the query sequence.

Computer programs are also available to determine the likelihood of certain polypeptides to form structures such as β-sheets. One such program, described herein, is the "ALB" program for protein and polypeptide secondary structure calculation and predication. In addition, secondary protein structure can be predicted from the primary amino acid sequence, for example using protein crystal structure and aligning the protein sequence related to the crystal structure (e.g., using Molecular Operating Environment (MOE) programs available from the Chemical Computing Group Inc., Montreal, P.Q., Canada). Other methods of predicting secondary structures are described, for example, in Garnier et al. (1996) *Methods Enzymol.* 266:540-553; Geourjon et al. (1995) *Comput. Applic. Biosci.* 11:681-684; Levin (1997) *Protein Eng.* 10:771-776; and Rost et al. (1993) *J. Molec. Biol.* 232:584-599.

Homology can also be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences may exhibit at least about 80%-85%, preferably at least about 90%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence that "encodes" a selected protein, is a nucleic acid sequence that is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic and semisynthetic DNA sequences and sequences including base analogs. A transcription termination sequence may be located 3' to the coding sequence.

"Control elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control elements need always be present so long as the desired gene is capable of being transcribed and translated.

A control element "directs the transcription" of a coding sequence in a cell when RNA polymerase will bind the promoter sequence and transcribe the coding sequence into mRNA, which is then translated into the polypeptide encoded by the coding sequence.

"Operably linked" refers to an arrangement of elements wherein the components so described are configured so as to perform their usual function. Thus, control elements operably linked to a coding sequence are capable of effecting the expression of the coding sequence when RNA polymerase is present. The control elements need not be contiguous with the coding sequence, so long as they function to direct the expression thereof. Thus, for example, intervening untranslated yet transcribed sequences can be present between, e.g., a promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to fluorescein, rhodamine, dansyl, umbelliferone, Texas red, luminol, acradinium esters, NADPH, beta-galactosidase, horseradish peroxidase, glucose oxidase, alkaline phosphatase and urease.

Overview

The present invention concerns fusion proteins comprising CD4 mini-proteins, complexes of these fusion proteins with HIV Env polypeptides, as well as methods of making and using these fusion proteins and complexes. Without being bound by a particular theory, it appears that it has been difficult to generate immunological responses against Env because the CD4 binding site (and/or the CCR binding site) is buried between the outer domain, the inner domain and the V1/V2 domains of Env. Thus, although deletion of the V1/V2 domain may render the virus more susceptible to neutralization by monoclonal antibody directed to the CD4 site, the conformation of Env prior to CD4 binding may prevent an antibody response. Furthermore, when full length or near full length CD4 (e.g., soluble CD4 or sCD4) is used to induce the conformational change in Env, the immune system also mounts a response to the non-bound portions of CD4.

Thus, the present invention provides fusion proteins in which fragments of CD4 that bind to HIV Env polypeptides are contained in a fusion protein. The overall structure of the fusion protein preferably mimics a native CD4 conformation but does not include non-binding CD4 epitopes that may elicit unwanted immune responses. Thus, the non-CD4 heterologous regions are selected for structural similarity to native CD4 and/or for their ability to act as immunogens and/or immunomodulatory factors. Thus, these fusion proteins cause a conformational change in Env that exposes one or more epitopes (e.g., cryptic epitopes) in or near the CD4 binding site, which in turn allows the generation of an immune response (e.g., a neutralizing antibody response) to Env without the unwanted immune response to CD4.

Various forms of the different embodiments of the invention, described herein, may be combined:

CD4 Minimal Modules

In the practice of the present invention, Env polypeptides are complexed to fusion proteins comprising a CD4 minimal module in order to change conformation of the Env polypeptide and expose epitopes that elicit neutralizing antibodies.

The amino acid sequence of CD4 is known (FIG. 1) and structural studies on CD4 have shown that this molecule is composed of four extracellular immunoglobulin-like domains (three containing disulfide linked loops). It is also known that the binding of gp120 to its receptor (CD4) induces conformational changes in the Env protein. However only domain 1 (D1) of CD4 is critical for its interaction with gp120 (Arthos et al. (1989) Cell 57(3):469-481; Truneh et al. (1991) J Biol Chem 266(9):5942-5948). Mutational analyses, antibody competition experiments combined with the knowledge of three-dimensional structure of CD4 have shown that a region homologous to complementarity determining region 2 (CDR2) of immunoglobulin in D1 plays a major role in gp120 binding (Ryu et al. (1994) Structure 2(1):59-74, Sullivan et al. (1998) J Virol 72(8):6332-6338). Indeed, structure resolution of gp120:CD4 complex confirmed that the CDR2-like loop of CD4 is central in CD4-gp120 interaction (Choe & Sodroski (1992) J Acquir Immune Defic Syndr 5(2):204-210, Gizachew et al. (1998) Biochemistry 37(30):10616-10625).

Crystallographic structure analysis of gp120, in complex with CD4 and the Fab portion the neutralizing monoclonal antibody 17b (Kwong et al. (1998) Nature 393:648-659), indicates that a large surface (742 Å2) of the domain D1 of CD4 binds to a large depression (800 Å2) on gp120. The CD4 interface is comprised by 22 residues, contributing to gp120 binding with mixed hydrophobic, electrostatic, H-bonding interactions. The large size and complexity of this interface makes the reproduction of such functional epitope into a small molecule a challenge, and explains the difficulty in the development of small molecule inhibitors of gp120-CD4 interaction. Vita et al. (1998) *Biopolymers* 47:93-100. However, in spite of the large number of residues present in gp120-CD4 interaction surface, studies on hormone-receptor systems showed that only a few residues might dominate the binding energy at the protein-protein interface. Clackson and Wells (1995) *Science* 267(5196):383-386.

Upon binding of gp120 to CD4, unique neutralizing epitopes also appear to be exposed, for example the epitope recognized by the monoclonal antibody CG10 (Gershoni et al. (1993) *Faseb J* 7(12):1185-1187). Indeed, while monomeric gp120 protein from lab strains is poorly immunogenic with regard to eliciting primary isolate neutralizing antibodies (Mascola et al. (1996) *J. Infect. Dis.* 173:340-348), monoclonal antibodies that appear to recognize certain epitopes that are exposed on the Env surface once it binds to its CD4 receptor have been shown to neutralize diverse primary isolates. See, e.g., the antibody designated 17b (Thali et al. (1993) J Virol 67(7):3978-3988). However, cross-clade primary isolate neutralizing antibody responses using receptor/co-receptor complexed Env have been attributed to the immunogenicity of the gp41 fusion domain. Lacasse et al (1999) *Science* 283:357-362.

Additionally, attempts to evaluate gp120-CD4 complexes as potential vaccine candidate for inducing high avidity and primary isolate neutralizing antibodies have been thwarted by the concern that an immune response could be generated against CD4 itself thereby raising autoimmune and safety issues. (D'Souza et al. (1997) *J Infect Dis.* 175:1056-1062, DeVico et al. (1995) *Virology* 211(2):583-588).

Thus, the present invention makes use of less than full-length CD4 proteins or derivatives thereof that are contained within fusion proteins comprising non-CD4 proteins or polypeptides. The fusion proteins preferably bind to, or are complexed to, an Env protein via the CD4 minimal module. In certain embodiments, the CD4 minimal module portion of the fusion protein comprises amino acid residues 15-85 of SEQ ID NO:1 or a molecule that exhibits structural similarity to a CD4 minimal module (e.g., a CD4 mimetic as described for example in Martin et al. (2003) Nat. Biotech. 21(1):71-76). Structural similarity can be determined as described herein. As shown in FIG. 4, a CD4 mini protein comprising residues 15-85 of SEQ ID NO:1 is almost completely buried within the gp120 binding pocket. In addition, this CD minimal module is stabilized by the presence of a disulfide bridge between Cys16 and Cys84.

One of skill in the art can readily determine amino acid sequences that exhibit structural and/or amino acid similarity to the CD4 minimal modules described herein in view of the specification. Further, any of these homologs (structural or sequence), can be further modified. Such modifications can affect structure and/or function. For example, amino acid substitutions, additions and/or deletions can be made to the mini-proteins such that the gp120 binding structure is preserved or enhanced.

Any of the CD4 molecules useful in the practice of the invention can be chemically synthesized. Preferably, the synthesis is conducted under conditions that allow and promote efficient folding of the mini-protein into a conformation that binds gp120 and exposes epitopes in or near the CD4 binding site. For example, the mini-protein can be synthesized under conditions that produce a circular dichroism spectrum similar to that of CD4, in spite of mutations in the native sequence.

Heterologous (Non-CD4) Polypeptides

In order to improve the stability of CD4 minimal modules as described herein, the minimal modules are expressed as fusion protein within heterologous sequences exhibiting a compatible tertiary structure to native CD4. In this way, the binding of the CD4 minimal module to Env is enhanced while reducing unwanted immune responses to non-Env binding regions of CD4. Proteins exhibiting structural similarity to wild-type CD4 were identified by performing searches of structural databases, as described herein.

In order to minimize the risk of undesired autoimmunity, it is preferred that the heterologous sequences be obtained from non-human or non-primate proteins. In addition, proteins exhibiting high homology to human proteins at the amino acid level are preferably not used.

Figure 5:
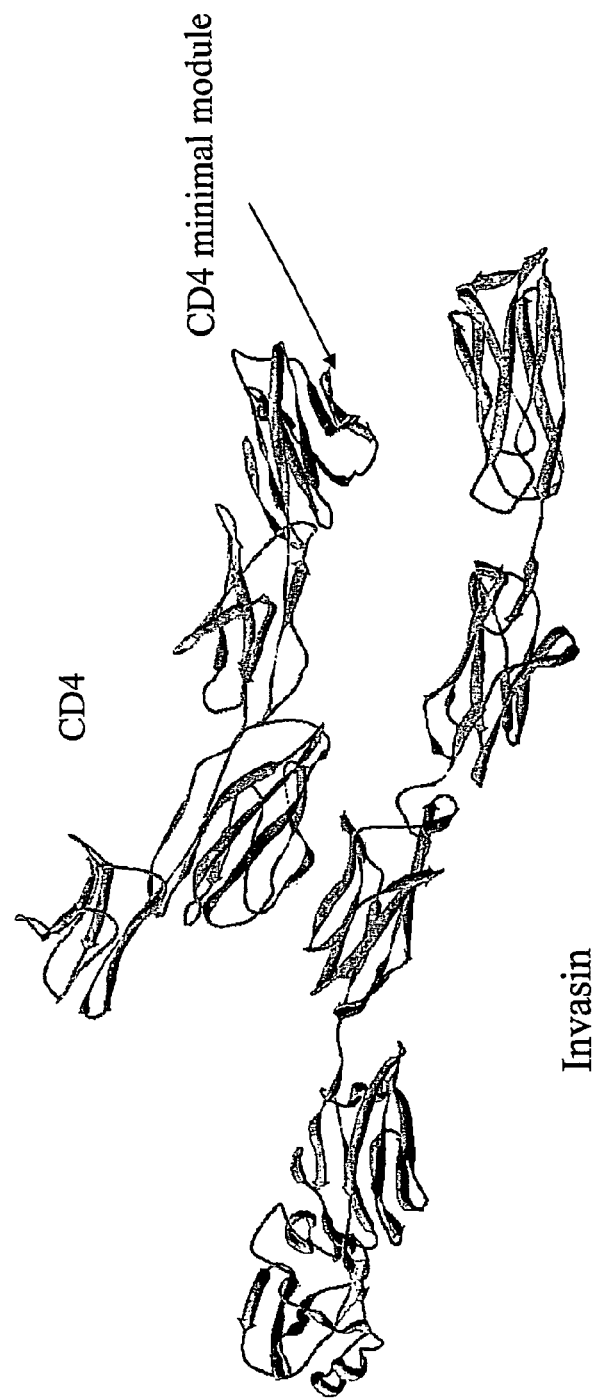

An exemplary protein having a similar overall tertiary structure in one or more regions to CD4 is shown in FIG. 5. In particular, invasin (FIG. 2, SEQ ID NO:2) from *Yersinia pseudotuberculosis* has an Ig-like architecture similar to CD4. *Yersinia pseudotuberculosis* has a N-terminal transmembrane domain followed by five extracellular domains (D1-D5). The first four domains (D1 to D4) are predominantly β stranded and have an Ig-like conformation. The fifth domain has interspersed α helical and β-stranded regions related to C-type lectin-like domains.

In addition to conformational features, the non-CD4 portion(s) of the fusion protein can be selected for other characteristics, for example immunogenicity, adjuvanticity and/or immunomodulatory characteristics. Invasin, for instance, is known to stimulate cellular immune responses. See, e.g., Fortineau et al. (1994) *Clin Diagn Lab Immunol.* 1(2):235-237; Ennis et al. (1993) *J Exp Med.* 177(1):207-212. The immunogenic nature of invasin may also serve to adjuvant the antibody response to the exposed Env epitopes.

Non-limiting examples of fragments of invasin are shown in FIGS. 2B to 2J and include residues 737-751 of SEQ ID NO:2 (shown in FIG. 2B and SEQ ID NO:5), which may be used to replace residues 1-14 of native CD4. Residues 584-595 of SEQ ID NO:2 (shown in FIG. 2C and SEQ ID NO:6) may be used to replace residues 86-98 of a native CD4). Other fragments of invasin that may be used include domain 1 (D1, residues 503-595 of SEQ ID NO:2, shown in FIG. 2D and SEQ ID NO:7), domain 2 (D2, residues 596-694 of SEQ ID NO:2, shown in FIG. 2E and SEQ ID NO:8), domain 3 (D3, residues 695-795 of SEQ ID NO:2, shown in FIG. 2F and SEQ ID NO:9), and domain 4 (D4, residues 796-888 of SEQ ID NO:2, shown in FIG. 2G and SEQ ID NO:10). FIGS. 2H, 2I and 2J (SEQ ID NOs:11, 12 and 13, respectively), show combinations of polypeptides comprising fragments of invasin, including D1 and D2 (FIG. 2H, SEQ ID NO:11); D1, D2 and D3 (FIG. 2I, SEQ ID NO:12); and D1, D2, D3, and D4 (FIG. 2J, SEQ ID NO:13). It will be apparent that other fragments may be used and, in addition, that the fragments used may be in different orders than they occur in native invasin (e.g., D1 may be flanked by D2, D3 and/or D4). The fragments used may also include additional residues, for example linkers or the like. Furthermore, the fragments may include one or more additions, deletions and/or substitutions (e.g., peptoid substitutions) as compared to wild-type, so long as the overall tertiary structure remains the same.

Figure 7:

Accordingly, fusion molecules were designed comprising the CD4 minimal module in a scaffold provided by various fragments of invasin. FIGS. 7 and 8 show exemplary fusion proteins disclosed herein. See, also, Example 1. The protein shown in FIG. 7 includes from N-terminus to C-terminus the following polypeptides: residues 737-751 of invasin (replacing residues 1-14 of CD4); residues 15-85 of CD4 (CD4 minimal module); residues 584-595 of invasin (replacing residues 86-98 of CD4); and residues 506 to 986 of invasin (replacing residues 99-433 of CD4).

FIG. 8A shows another exemplary protein that includes, from N-terminus to C-terminus the following polypeptides: residues 737-751 of invasin (replacing residues 1-14 of CD4, depicted with stripes); residues 15-85 of CD4 (dark gray); residues 584-595 of invasin (replacing residues 86-98 of CD4, shown as stippled bars); and residues 503 to 595 of invasin (light gray).

FIG. 8B shows another exemplary protein that includes, from N-terminus to C-terminus the following polypeptides: residues 737-751 of invasin (replacing residues 1-14 of CD4, depicted with stripes); residues 15-85 of CD4 (dark gray); residues 584-595 of invasin (replacing residues 86-98 of CD4, shown as stippled bars); and residues 503 to 694 of invasin (light gray).

FIG. 8C shows another exemplary protein that includes, from N-terminus to C-terminus the following polypeptides: residues 737-751 of invasin (replacing residues 1-14 of CD4, depicted with stripes); residues 15-85 of CD4 (dark gray); residues 584-595 of invasin (replacing residues 86-98 of CD4, shown as stippled bars); and residues 503 to 795 of invasin (light gray).

FIG. 8D shows yet another exemplary protein that includes, from N-terminus to C-terminus the following polypeptides: residues 737-751 of invasin (replacing residues 1-14 of CD4, depicted with stripes); residues 15-85 of CD4 (dark gray); residues 584-595 of invasin (replacing residues 86-98 of CD4, shown as stippled bars); and residues 503 to 888 of invasin (light gray).

As noted above, it will be apparent that that one or more invasin fragments can be substituted with other polypeptides exhibiting similar structural characteristics.

The fusion proteins described herein may also further comprise additional non-CD4 polypeptides including, but not limited to, antigenic polypeptides from one or more pathogens (e.g., viruses such as HIV, HBC, HCV, HAV, RSV, influenza etc or bacteria), immunomodulatory polypeptides such as cytokines, chemokines and the like. For example, the fusion protein may include the Env polypeptide to which the CD4 minimal module is capable of binding. In this way, a single fusion protein can function as an Env-CD4 minimal module complex to expose epitopes revealed by CD4 binding. Additional HIV polypeptides may also be included in the fusion protein, for example one or more of Gag, Pol, Prot, Nef Rev, Tat, Vpu, Vpr, Vif or immunogenic fragments thereof.

Env Polypeptides

The Env polypeptide portion of the complexes described herein can be derived from an envelope protein, preferably from HIV Env. As noted above, the envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides.

In certain embodiments, the Env polypeptide component of the complex is a monomer or a dimer. In preferred embodiments, the Env polypeptide component is an oligomeric Env polypeptide. The primary sequence of the Env polypeptide precursor of HIV-1$_{SF2}$ (hereinafter "SF2") strain is known. See, e.g., FIG. 1 of International Publication No. WO04/037847. The gp120 amino acid sequence (including leader sequence) extends from approximately amino acids 1-509. The polypeptide contains approximately 24 N-linked glycosylation sites that are common to most, if not all, gp120 sequences. As suggested by their name, the hypervariable domains contain extensive amino acid substitutions, insertions and deletions as between strains. Despite this variation, most, if not all, Env polypeptide sequences preserve the virus's ability to bind to the viral receptor CD4. Further, alignment of the amino acid sequences of Env polypeptide of any HIV variant can be determined relative to other variants, such as HXB-2, as described for example, in WO 00/39303. In other embodiments, the Env polypeptide comprises an oligomeric form of Env, for example oligomeric gp140 (o-gp140).

The Env polypeptide bound or complexed to the fusion proteins described herein can be derived any known HIV isolates, as well as newly identified isolates, and subtypes of these isolates. Descriptions of structural features can be given herein with reference to SF2 or HXB-2. One of ordinary skill in the art in view of the teachings of the present disclosure and the art can determine corresponding regions in other HIV variants (e.g., isolates HIV$_{IIIb}$, HIV-1$_{SF162}$, HIV-1$_{SF170}$, HIV$_{LAV}$, HIV$_{MN}$, HIV-1$_{CM235}$, HIV-1$_{US4}$, other HIV-1 strains from diverse subtypes (e.g., subtypes, A through G, and O), HIV-2 strains and diverse subtypes (e.g., HIV-2$_{UC1}$ and HIV-2$_{UC2}$), and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify n-sheet regions). The actual amino acid sequences of the Env polypeptides can be based on any HIV variant.

As with the fusion proteins, the Env polypeptides bound by and/or used in complexes with the fusion proteins described herein may include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes; such capability must be retained. The Env polypeptides described herein can be monomeric or oligomeric.

Polypeptide Production

The CD4 molecules (e.g., CD4 mini-proteins), non-CD4 heterologous proteins and polypeptides, Env polypeptides and fusion molecules of the present invention can be produced in any number of ways all of which are well known in the art.

In one embodiment, the polypeptides are generated using recombinant techniques, well known in the art. In this regard, oligonucleotide probes can be devised based on the known sequences of the polypeptide of interest and used to probe genomic or cDNA libraries for the gene(s) encoding the polypeptide. The gene can then be further isolated using standard techniques and, e.g., restriction enzymes employed to truncate the gene at desired portions of the full-length sequence. Similarly, the gene(s) can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The genes encoding the components of the fusion proteins and/or Env polypeptides can be produced synthetically, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone a gene encoding a selected polypeptide gene that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci. USA* (1982) 79:6409.

Once coding sequences for the desired polypeptides have been isolated or synthesized, they can be cloned into any suitable vector or replicon for expression. As will be apparent from the teachings herein, a wide variety of vectors encoding polypeptides and/or fusion proteins can be generated by creating expression constructs which operably link, in various combinations, polynucleotides encoding CD4 mini proteins and heterologous sequences. Non-limiting examples of such combinations are discussed in the Examples.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insert cell expression systems are commercially available in kit form from, inter alia, Invitrogen, San Diego Calif.

Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601.

Similarly, bacterial and mammalian cell expression systems are also known in the art and described in, e.g., *Yeast Genetic Engineering* (Barr et al., eds., 1989) Butterworths, London.

Plant expression systems can also be used to produce the proteins described herein. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431, 739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (e.g., Hep G2), Madin-Darby bovine kidney ("MDBK") cells, as well as others. Mammalian sources of cells include, but are not limited to, human or non-human primate (e.g., PERC.6 cells which are described, for example, in WO 01/38362 and WO 02/40665, as well as deposited under ECACC deposit number 96022940), MRC-5 (ATCC CCL-171), WI-38 (ATCC CCL-75), fetal rhesus lung cells (ATCC CL-160), human embryonic kidney cells (293 cells, typically transformed by sheared adenovirus type 5 DNA), VERO cells from monkey kidneys), horse, cow (e.g., MDBK cells), sheep, dog (e.g., MDCK cells from dog kidneys, ATCC CCL34 MDCK (NBL2) or MDCK 33016, deposit number DSM ACC 2219 as described in WO 97/37001), cat, and rodent (e.g., hamster cells such as BHK21-F, HKCC cells, or Chinese hamster ovary cells (CHO cells)), and may be obtained from a wide variety of developmental stages, including for example, adult, neonatal, fetal, and embryo.

Avian sources of cells include, but are not limited to, chicken cells (e.g., chicken embryonic stem cells (e.g., EBx® cells), chicken embryonic fibroblasts, chicken embryonic germ cells)). Similarly, bacterial hosts such as *E. coli, Bacillus subtilis*, and *Streptococcus* spp., will find use with the present expression constructs. Yeast hosts useful in the present invention include, inter alia, *Saccharomyces cerevisiae, Candida albicans, Candida maltosa, Hansenual polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, for example for the production of an Env polypeptide, the transformed cells secrete the polypeptide product into the surrounding media. Certain regulatory sequences can be included in the vector to enhance secretion of the protein product, for example using a tissue plasminogen activator (TPA) leader sequence, an interferon (γ or α) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

In another embodiment, the transformed cells are disrupted, using chemical, physical or mechanical means, which lyse the cells yet keep the polypeptides (e.g., Env) substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular Env polypeptides of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the polypeptides can be further purified using conventional techniques well known in the art, such as by any of the techniques described above.

Relatively small polypeptides, i.e., up to about 50 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides:*

*Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptide analogs of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Env-Fusion Protein Complexes

Env and the CD4 minimal module-containing molecules described herein can be complexed in a variety of ways. In certain embodiments, Env and the fusion molecule are complexed using one or more cross-linking agents or fixatives, such as formaldehyde, formalin, glutyraldehyde and the like. In other embodiments, a CD4 miniprotein-containing fusion protein is linked to the envelope by a specific covalent bond which will not perturb the envelope exposed antigenic surface, yet exposing the cryptic conserved epitopes that are normally not accessible, for example so that an antibody response can be mounted. CD4 minimal module-containing molecules are cross-linked with Env to maintain the exposure of CD4-inducible epitopes in the Env protein for immunization purposes to target the functional epitopes for vaccine applications.

In addition, suitable complexes may be produced by e.g., co-transfecting host cells with constructs encoding the fusion proteins described herein and/or one or more Env polypeptides. In certain embodiments, the Env polypeptides are part of the fusion protein. Thus, co-transfection can be accomplished either in trans or cis, i.e., by using separate vectors or by using a single vector that bears both of the Env and the CD4 mini-protein-containing fusion protein. If done using a single vector, both genes can be driven by a single set of control elements. In another embodiment, the Env- and fusion protein-encoding sequences can be present on the vector in individual expression cassettes, driven by individual control elements. Following expression, the proteins may spontaneously associate. In another embodiment, the complexes can be formed by mixing the individual proteins together which have been produced separately, either in purified or semi-purified form, or even by mixing culture media in which host cells expressing the proteins, have been cultured. See, International Publication No. WO 96/04301 for a description of such complexes.

Antibodies

Antibodies, both monoclonal and polyclonal, which are directed against Env-fusion molecule complexes epitopes (and cryptic epitopes exposed by binding of CD4 to Env) are particularly useful in diagnosis and therapeutic applications, for example, those antibodies which are neutralizing are useful in passive immunotherapy. Monoclonal antibodies, in particular, may be used to raise anti-idiotype antibodies.

Anti-idiotype antibodies are immunoglobulins that carry an "internal image" of the antigen of the infectious agent against which protection is desired. Techniques for raising anti-idiotype antibodies are known in the art. See, e.g., Grzych (1985), Nature 316:74; MacNamara et al. (1984), Science 226:1325, Uytdehaag et al (1985), J. Immunol. 134: 1225. These anti-idiotype antibodies may also be useful for treatment and/or diagnosis of HIV.

An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens or a combination of monoclonal and polyclonal antibodies.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays which amplify the signals from the probe are also known. Examples of which are assays which utilize biotin and avidin, and enzyme-labeled and mediated immunoassays, such as ELISA assays.

An enzyme-linked immunosorbent assay (ELISA) can be used to measure either antigen or antibody concentrations. This method depends upon conjugation of an enzyme to either ah antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated colorimetrically, and related to antigen concentration.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against epitopes exposed by binding of CD4 to Env can also be produced. Normal B cells from a mammal, such as a mouse, immunized with, e.g., an Env-CD4 complex as described herein can be fused with, for example, HAT-sensitive mouse myeloma cells to produce hybridomas. Hybridomas producing antibodies specific for epitopes exposed when CD4 miniproteins bind to Env can be identified using RIA or ELISA and isolated by cloning in semi-solid agar or by limiting dilution. Clones producing the desired specific antibodies are isolated by another round of screening. Antibodies, either monoclonal and polyclonal, which are directed against epitopes, are particularly useful for detecting the presence of antigens in a sample, such as a serum sample from an HIV-infected human. An immunoassay for an HIV antigen may utilize one antibody or several antibodies. An immunoassay for an HIV antigen may use, for example, a monoclonal antibody directed towards an HIV epitope, a combination of monoclonal antibodies directed towards epitopes of one Env or Env-CD4 minimal module-containing fusion polypeptide, monoclonal. antibodies directed towards epitopes of different polypeptides, polyclonal antibodies directed towards the same HIV antigen, polyclonal antibodies directed towards different HIV antigens, or a combination of monoclonal and Polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate Env or fusion protein complexed-Env by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind the target from a biological sample, such as blood or plasma. The bound proteins or complexes are recovered from the column matrix by, for example, a change in pH.

Diagnostic, Vaccine and Therapeutic Applications

The fusion molecules and complexes comprising these fusion molecules (e.g., complexes with Env) of the present invention or the polynucleotides coding therefor, can be used for a number of diagnostic and therapeutic purposes. For example, the proteins and polynucleotides or antibodies generated against the same, can be used in a variety of assays, to determine the presence of reactive antibodies/and or Env proteins in a biological sample to aid in the diagnosis of HIV infection or disease status or as measure of response to immunization.

As noted above, the presence of antibodies reactive with the Env (e.g., gp120) polypeptides and, conversely, antigens reactive with antibodies generated thereto, can be detected using standard electrophoretic and immunodiagnostic techniques, including immunoassays such as competition, direct reaction, or sandwich type assays. Such assays include, but are not limited to, western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigen and the antibody or antibodies reacted therewith.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like.

Typically, the solid support is first reacted with the biological sample (or the gp120 proteins), washed and then the antibodies, (or a sample suspected of containing antibodies), applied. After washing to remove any non-bound ligand, a secondary binder moiety is added under suitable binding conditions, such that the secondary binder is capable of associating selectively with the bound ligand. The presence of the secondary binder can then be detected using techniques well known in the art. Typically, the secondary binder will comprise an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal.

In another embodiment, a "two antibody sandwich" assay can be used to detect the proteins of the present invention. In this technique, the solid support is reacted first with one or more of the antibodies directed against Env (e.g., gp120), washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the viral proteins and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The complexes described herein, produced as described above, or antibodies to the complexes, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The complexes and polynucleotides encoding the polypeptides can also be used in vaccine compositions, individually or in combination, in e.g., prophylactic (i.e., to prevent infection) or therapeutic (to treat HIV following infection) vaccines. The vaccines can comprise mixtures of one or more of the modified Env proteins (or nucleotide sequences encoding the proteins), such as Env (e.g., gp120) proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125-ser125), GM-CSF, IL-12, -interferon, IP-10, MIP1 and RANTES. The vaccines may be administered as polypeptides or, alternatively, as naked nucleic acid vaccines (e.g., DNA), using viral vectors (e.g., retroviral vectors, alphaviral vectors, adenoviral vectors, adeno-associated viral vectors) or non-viral vectors (e.g., liposomes, particles coated with nucleic acid or protein, including viral replicon particles). The vaccines may also comprise a mixture of protein and nucleic acid, which in turn may be delivered using the same or different vehicles. The vaccine may be given more than once (e.g., a "prime" administration followed by one or more "boosts") to achieve the desired effects. The same composition can be administered as the prime and as the one or more boosts. In another embodiment, different compositions can be used for priming and boosting.

A number of viral based systems have been developed for delivery and administration of nucleic acid molecules into mammalian cells. For example, retroviruses provide a convenient platform for nucleic acid delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, (1989) *Bio Tech.* 7:980-990; Miller, A. D., (1990) *Hum. Gene Ther.* 1:5-14; Scarpa, et al., (1991) *Virol.* 180:849-852; Burns, et al. (1993) *Proc. Natl. Acad. Sci. USA* 90:8033-8037; and Boris-Lawrie and Temin (1993) *Curr. Opin. Genet. Develop.* 3:102-109.

A number of adenovirus vectors have also been described for nucleic acid delivery. Unlike retroviruses which integrate into the host genome, adenoviruses persist extrachromosomally thus minimizing the risks associated with insertional mutagenesis (Haj-Ahmad and Graham, (1986) *J. Virol.* 57:267-274; Bett, et al., (1993) *J. Virol.* 67:5911-5921; Mittereder, et al., (1994) *Hum. Gene Ther.* 5:717-729; Seth, et al., (1994) *J. Virol.* 68:933-940; Barr, et al., (1994) *Gene Therapy* 1:51-58; Berkner, K. L., (1988) *BioTech.* 6:616-629; and Rich, et al., (1993) *Hum. Gene Ther.* 4:461-476).

Additionally, various adeno-associated virus (AAV) vector systems have been developed for nucleic acid delivery and administration. AAV vectors can be readily constructed using techniques well known in the art. See, e.g., U.S. Pat. Nos. 5,173,414 and 5,139,941; WO 92/01070; WO 93/03769; Lebkowski, et al. (1988) *Mol. Cell. Biol.* 8:3988-3996; Vincent, et al., (1990) *Vaccines* 90 (Cold Spring Harbor Laboratory Press); Carter, B. J., (1992) *Curr. Opin. Biotech.* 3:533-539; Muzyczka, N., (1992) *Curr. Top. Microbiol. Immunol.* 158:97-129; Kotin, R. M., (1994) *Hum. Gene Ther.* 5:793-801; Shelling and Smith, (1994) *Gene Ther.* 1:165-169; and Thou, et al., (1994) *J. Exp. Med.* 179:1867-1875.

Another vector system useful for delivering polynucleotides is the enterically administered recombinant poxvirus vaccines described by Small, Jr., P. A., et al. (U.S. Pat. No. 5,676,950).

Additional viral vectors which will find use for delivery and administration of nucleic acid molecules include those derived from the pox family of viruses, including vaccinia virus and avian poxvirus. In another embodiment, avipoxviruses, such as the fowlpox and canarypox viruses, can also be used for delivery of nucleic acid molecules. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael, et al., (1993) *J. Biol. Chem.* 268:6866-6869 and Wagner, et al., (1992) *Proc. Natl. Acad. Sci. USA* 89:6099-6103, can also be used for nucleic acid delivery or administration.

Members of the Alphavirus genus, such as, but not limited to, vectors derived from the Sindbis, Semliki Forest, and Venezuelan Equine Encephalitis viruses, will also find use as viral vectors for delivery and administration of nucleic acid molecules. For a description of Sindbis-virus derived vectors see, e.g., Dubensky, et al., (1996) *J. Virol.* 70:508-519; WO 95/07995; WO 96/17072; U.S. Pat. No. 5,843,723; and U.S. Pat. No. 5,789,245. See also WO 02/099035; and U.S. Publication No. 2003/018262.

Viral replicon particles can be used for delivery and administration of nucleic acid and polypeptide molecules. For example, alphavirus replicon particles, including chimeric alphavirus replicon particles, can be used for delivery and administration of nucleic acid and polypeptide molecules. For a description of alphavirus replicon particle systems see, e.g., WO 02/099035; U.S. Publication No. 2003/018262; WO 96/37616; U.S. Publication No. 2003/0119182; WO 03/023026; and WO 05/016961.

Nucleic acid and polypeptide molecules can also be delivered without a viral vector. For example, nucleic acid and/or polypeptide molecules can be packaged in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, (1991) *Biochim. Biophys. Acta.* 1097:1-17; Straubinger, et al., (1983), *Meth. Enzymol.* 101:512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Feigner, et al., (1987) *Proc. Natl. Acad. Sci. USA* 84:7413-7416); mRNA (Malone, et al., (1989) *Proc. Natl. Acad. Sci. USA* 86:6077-6081); and purified transcription factors (Debs, et al., (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Feigner, et al., (1987) *Proc. Natl. Acad. Sci. USA* 84:7413-7416). Other commercially available lipids include (DDAB/DOPE) and DOTAP/DOPE (Boerhinger). Other cationic liposomes can be prepared from readily available materials using techniques well known in the art. See, e.g., Szoka, et al., (1978) *Proc. Natl. Acad. Sci. USA* 75:4194-4198; WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger, et al., (1983) *Meth. Immunol.* 101:512-527; Szoka, et al., (1978) *Proc. Natl. Acad. Sci. USA* 75:4194-4198; Papahadjopoulos, et al., (1975) *Biochim. Biophys. Acta* 394:483-491; Wilson, et al., (1979) *Cell* 17:77-84); Deamer and Bangham, (1976) *Biochim. Biophys. Acta* 443:629-634; Ostro, et al., (1977) *Biochem. Biophys. Res. Commun.*

76:836-842; Fraley, et al., (1979) *Proc. Natl. Acad. Sci. USA* 76:3348-3352); Enoch and Strittmatter, (1979) *Proc. Natl. Acad. Sci. USA* 76:145-149; Fraley, et al., (1980) *J. Biol. Chem.* 255:10431-10435; Szoka and Papahadjopoulos, (1978) *Proc. Natl. Acad. Sci. USA* 75:4194-4198; and Schaefer-Ridder, et al., (1982) *Science* 215:166-168.

The nucleic acid and/or polypeptide molecules can also be delivered in cochleate lipid compositions similar to those described by Papahadjopoulos, et al., (1975) *Biochem. Biophys. Acta.* 394:483-491. See, also, U.S. Pat. Nos. 4,663,161 and 4,871,488.

The nucleic acid and/or polypeptide molecules may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery, et al., (1993) *Pharm. Res.* 10:362-368; McGee, J P, et al., (1997) *J Microencapsul.* 14(2):197-210; O'Hagan D T, et al., (1993) *Vaccine* 11(2):149-154. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA (see, e.g., WO 00/06123). The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the Env polypeptide may be conjugated to a bacterial toxoid, such as toxoid from diphtheria, tetanus, cholera, etc.

Adjuvants may also be used to enhance the effectiveness of the vaccines. Adjuvants for use with the invention include, but are not limited to, one or more of the following set forth below:

A. Mineral Containing Compositions

Mineral containing compositions suitable for use as adjuvants include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of *Vaccine Design* . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included such that the dose of $Al^{3+}$ is between 0.2 and 1.0 mg per dose.

In one embodiment the aluminum based adjuvant is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another exemplary aluminum-based adjuvant is aluminum hydroxide adjuvant ($Al(OH)_3$) or crystalline aluminum oxyhydroxide (A100H), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment the adjuvant comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1; 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-Emulsions

Oil-emulsion compositions suitable for use as adjuvants include, but are not limited to, squalene-water emulsions, such as MF59 (5% Squalene, 0.5% Tween 80, and 0.5% Span 85, formulated into submicron particles using a microfluidizer). See WO90/14837. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:4234-4237. MF59 is used as the adjuvant in the FLUAD™ influenza virus trivalent subunit vaccine.

Particularly preferred adjuvants are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span 85' (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose.

As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants in the invention.

C. Saponin Formulations

Saponin formulations, may also be used as adjuvants. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621. A review of the development of saponin based adjuvants can be found in Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

D. Virosomes and Virus Like Particles (VLPs)

Virosomes and Virus Like Particles (VLPs) can also be used as adjuvants. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, QB-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomavirus-Like Particles Induce Acute Activation of Dendritic Cells", Journal of Immunology (2001) 5246-5355; Pinto, et al., "Cellular Immune Responses to Human Papillomavirus (HPV)-16 L1 Healthy Volunteers Immunized with Recombinant HPV-16 µl Virus-Like Particles", Journal of Infectious Diseases (2003) 188:327-338; and Gerber et al., "Human Papillomavirus Virus-Like Particles Are Efficient Oral Immunogens when Coadministered with *Escherichia coli* Heat-Labile Enterotoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10 B 16. Immunopotentiating reconstituted influenza virosomes (IRIV) are used as the subunit antigen delivery system in the intranasal trivalent INFLEXAL™ product {Mischler & Metcalfe (2002) *Vaccine* 20 Suppl 5:B17-23} and the INFLUVAC PLUS™ product.

E. Bacterial or Microbial Derivatives

Additional adjuvants include bacterial or microbial derivatives such as:

(1) Non-toxic derivatives of enterobacterial lipopolysaccharide (LPS) Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives: Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory oligonucleotides: Immunostimulatory oligonucleotides suitable for use as adjuvants include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31(part 3):664-658; Bhagat et al., "CpG penta- and hexadeoxyribonucleotides as potent immunomodulatory agents" BBRC (2003) 300:853-861 and WO03/035836.

(4) ADP-ribosylating toxins and detoxified derivatives thereof. Bacterial ADP-ribosylating toxins and detoxified derivatives thereof may be used as adjuvants. Preferably, the protein is derived from E. coli (i.e., E. coli heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR1920. The use of ADP-ribosylating toxins and detoxified derivatives thereof, particularly LT-K63 and LT-R72, as adjuvants can be found in the following references: Beignon, et al., "The LTR72Mutant of Heat-Labile Enterotoxin of Escherichia coli Enhances the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol. (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of Escherichia coli Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280; Partidos et al., "Heat-labile enterotoxin of Escherichia coli and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the Escherichia coli heat-labile enterotoxin as safe and strong adjuvants for intranasal delivery of vaccines", Vaccines (2003) 2(2):285-293; and Pine et al., (2002) "Intranasal immunization with influenza vaccine and a detoxified mutant of heat labile enterotoxin from Escherichia coli (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol. (1995) 15(6):1165-1167.

F. Bioadhesives and Mucoadhesives

Bioadhesives and mucoadhesives may also be used as adjuvants. Suitable bioadhesives include esterified hyaluronic acid microspheres (Singh et al. (2001). J. Cont. Rele. 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention. E.g. WO99/27960.

G. Microparticles

Microparticles may also be used as adjuvants. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. Nos. 6,090,406, 5,916,588, and EP 0 626 169.

I. Polyoxyethylene ether and Polyoxyethylene Ester Formulations

Additional adjuvants include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyld-isoglutamine (nor-MDP), and N-acetylmuramyl-1-alanyl-d-isoglutaminyl-1-alanine-2-(β-2'-dipalmitoyl-sn-glycero-3-hydroxyphosphoryloxy)-ethylamine MTP-PE).

L. Imidazoquinoline Compounds.

Examples of imidazoquinoline compounds suitable for use adjuvants include Imiquimod and its analogues, described further in Stanley, "Imiquimod and the imidazoquinolines: mechanism of action and therapeutic potential" Clin Exp Dermatol (2002) 27(7):571-577; Jones, "Resiquimod 3M", Curr Opin Investig Drugs (2003) 4(2):214-218; and U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612.

M. Thiosemicarbazone Compounds

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-α.

N. Tryptanthrin Compounds.

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following adjuvant compositions may be used in the invention:

(1) a saponin and an oil-in-water emulsion (WO99/11241);
(2) a saponin (e.g., QS21)+a non-toxic LPS derivative (e.g. 3dMPL) (see WO94/00153);
(3) a saponin (e.g., QS21)+a non-toxic LPS derivative (e.g. 3dMPL)+a cholesterol;
(4) a saponin (e.g. QS21)+3dMPL+IL-12 (optionally+a sterol) (WO98/57659);
(5) combinations of 3dMPL with, for example, QS21 and/or oil-in-water emulsions (See European patent applications 0835318, 0735898 and 0761231);
(6) SAF, containing 10% Squalane, 0.4% Tween 80, 5% pluronic-block polymer L121, and thr-MDP, either microfluidized into a submicron emulsion or vortexed to generate a larger particle size emulsion.
(7) Ribi™ system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DetoxI™); and
(8) one or more mineral salts (such as an aluminum salt)+a non-toxic derivative of LPS (such as 3dPML).
(9) one or more mineral salts (such as an aluminum salt)+an immunostimulatory oligonucleotide (such as a nucleotide sequence including a CpG motif).

O. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the Env-CD4 minimal module-containing fusion protein complexes, or further complexes of these complexes, or nucleotide sequences encoding the same, antibodies directed to these complexes and any other of the above-mentioned components, as needed. By "therapeutically effective amount" is meant an amount that will induce a protective immunological response in the uninfected, infected or unexposed individual to whom it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the complex selected and its mode of administration, among other factors. An appropriate effective amount can be readily determined by one of skill in the art. A "therapeutically effective amount" will fall in a relatively broad range that can be determined through routine trials.

Once formulated, the nucleic acid vaccines may be accomplished with or without viral vectors, as described above, by injection using either a conventional syringe or a gene gun, such as the Accell® gene delivery system (PowderJect Technologies, Inc., Oxford, England). Delivery of DNA into cells of the epidermis is particularly preferred as this mode of administration provides access to skin-associated lymphoid cells and provides for a transient presence of DNA in the recipient. Both nucleic acids and/or peptides can be injected or otherwise administered either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Design of a Fusion Protein Comprising a CD4 Minimal Module

Novel fusion proteins comprising the gp120 binding region of human CD4 were designed as follows. The crystal structure of CD4-gp120 was analyzed and a region of CD4 involved in gp120 binding was identified. In particular, the region corresponding to amino acid residues 15-85 of CD4 is almost completely buried within the gp120-binding pocket (FIG. 4). This fragment was termed a CD4 minimal module and the fragment is stabilized by the presence of a disulfide bridge between Cys16 and Cys84.

Structural databases were searched for proteins having an overall configuration similar to CD4 in order to identify suitable structural scaffold into which CD4 minimal modules can be inserted to from fusion proteins. A total of 212 structures with structural similarity to native CD4 were identified. In order to minimize the risk of undesired autoimmunity, proteins from humans and primates, as well as proteins showing sequence similarity to human proteins, were eliminated.

The extracellular domain of the bacterium *Yersinia pseudotuberculosis* invasin was selected. This protein consists of a N-terminal transmembrane domain followed by five extracellular domains (D1-D5). The first four domains (D1 to D4) are predominantly 13 stranded, each adopting an Ig-like topology. The fifth domain has interspersed a helical and (3-stranded regions related to C-type lectin-like domains. Invasin from *Yersinia pseudotuberculosis* was identified as having a global Ig-like architecture similar to CD4.

Figure 6:
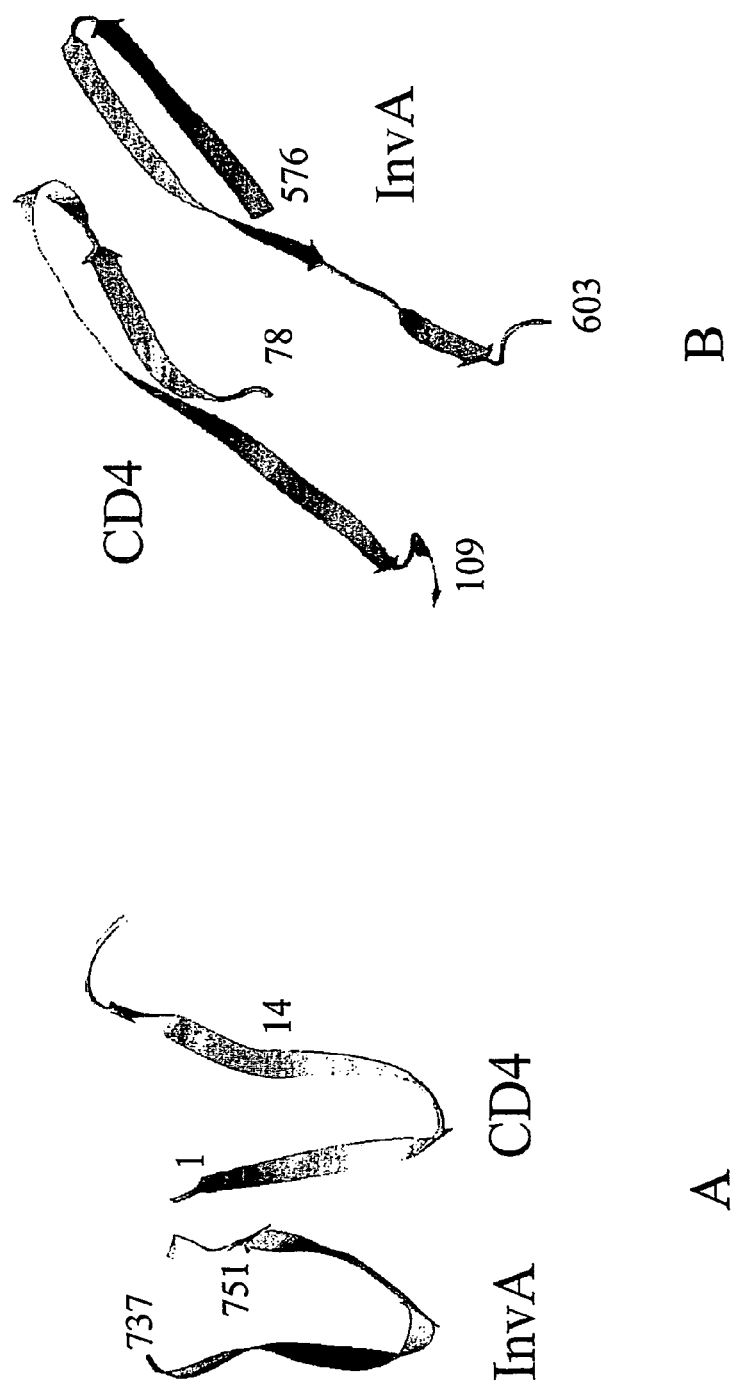

In addition, fragments of invasin were evaluated to determine structural similarity to residues 1-14 and 86 to 433 of CD4. FIG. 6 shows results of structural searches for these regions. These and additional results from structural searches showing compatible structures as between selected regions of CD4 and *Y. pseudotuberculosis* invasin are shown in Table 1:

TABLE 1

| CD4 amino acid residues | *Y. pseudotuberculosis* Invasin amino acid residues |
|---|---|
| 1-14 | GLN 737- SER 751 |
| 78-109 | THR 576- SER 603 |
| 86-98 | GLY 584- LYS 595 |
| 99-110 | THR 506 - ASN 517 |
| 111-121 | LYS 519 - ALA 529 |
| 122-136 | LEU 536 - LEU 550 |
| 137-141 | ASN 552 - GLU 556 |
| 142-146 | ALA 564 - LEU 568 |
| 149-152 | ASN 570 - ASP 573 |
| 154-163 | GLY 574 - GLU 583 |
| 166-181 | GLY 584 - ALA 599 |

Thus, residues 99-181 of CD4 include multiple regions that are structurally similar to residues 506-599 of invasin.

Subsequently, standard molecular biological techniques were used to clone the CD4 minimal module (residues 15-85) into various expression cassettes. The expression cassettes included sequences encoding multiple regions of invasin.

In particular, as shown in FIG. 7, one expression cassette included sequences encoding, in a 5'-3' direction, residues 737-751 of invasin, residues 15-85 of CD4 (CD4 minimal module), residues 584-595 of invasin, and residues 506 to 986 of invasin.

FIG. 8A-D show further expression cassettes. The expression cassette shown in FIG. 8A includes sequences, in a 5' to 3' direction, encoding residues 737-751 of invasin, residues 15-85 of CD4 (CD4 minimal module), residues 584-595 of invasin, and residues 503 to 595 of invasin. The expression cassette shown in FIG. 8B includes sequences, in a 5' to 3' direction, encoding residues 737-751 of invasin, residues 15-85 of CD4 (CD4 minimal module), residues 584-595 of invasin, and residues 503 to 694 of invasin. FIG. 8C shows an expression cassette comprising sequences (5' to 3' direction) encoding residues 737-751 of invasin, residues 15-85 of CD4 (CD4 minimal module), residues 584-595 of invasin, and residues 503 to 795 of invasin. FIG. 8D shows an expression cassette comprising sequences (5' to 3' direction) encoding residues 737-751 of invasin, residues 15-85 of CD4 (CD4 minimal module), residues 584-595 of invasin, and residues 503 to 888 of invasin.

When expressed, the fusion protein includes the Env binding site of CD4 in a structural scaffold that mimics the overall CD4 structure without providing unwanted CD4 epitopes.

Example 2

Expression of Invasin-CD4 Fusion Proteins

Expression cassettes encoding invasin-CD4 fusion proteins shown in FIGS. 2G, 2H, 2I and 2J were expressed in *E. coli*. Three hours after induction with 1 mm IPTG, total cell lysate and soluble fractions were prepared and run on SDS-PAGE (4-12% MES) gels. The constructs shown in FIGS. 2H, 2I and 2J (SEQ ID NOs:11, 12 and 13, respectively) expressed proteins of the expected molecular weights in the soluble fraction.

Subsequently, expression cassettes encoding the invasin-CD4 fusion proteins shown in FIGS. 2H, 2I and 2J (SEQ ID NOs:11, 12 and 13, respectively) were expressed in bacteria (*E. coli*), grown to high density and induced with 1 mM IPTG. Before induction, an uninduced sample was collected for evaluation. Following three hours of induction, cells were collected by centrifugation, lysed in lysis buffer and analyzed by SDS-PAGE/coomassie blue staining.

Proteins of the expected molecular weights were present in both induced and uninduced samples for all three constructs. Thus, invasin-CD4 fusion proteins can be expressed from expression cassettes.

Protein from crude cell lysates obtained after induction and cell lysis was optionally purified by affinity chromatography.

Example 3

Binding Characteristics

The binding characteristics of various invasin-CD4 fusion molecules and complexes comprising these molecules were evaluated as follows.

A. Binding by CD4 Antibodies

Proteins expressed as described in Example 2 were subject to Western blotting using anti-CD4 monoclonal and polyclonal antibodies developed in-house. Briefly, different fractions of cell lysates and purified proteins (supernatant, pellet, flow through) were run on a standard SDS-PAGE gel and transferred to a nitrocellulose membrane. The members were probes with anti-CD4 monoclonals and polyclonal and the blot developed using commercially available anti-mouse and anti-rabbit IgG. Blots were scanned using Odyssey® Infrared Imaging System (LI-COR Biosciences).

The invasin-CD4 fusion proteins tested were not detectable using the anti-CD4 monoclonals and polyclonals used in these experiments.

B. Binding to gp120

Supernatants, containing the proteins expressed as described in Example 2, were tested by surface plasmon resonance (BIAcore) for binding to gp120 and monoclonal antibody 48D (which binds to an epitope exposed when CD4 is bound to Env, see, e.g., Wyatt et al. (1995) *J. Virol.* 69(9): 5723-5733, provided by Dr. James Robinson, Department of Pediatrics, Tulane University).

In addition to the supernatant obtained from cell lysates, crude bacterial extracts obtained after induction and lysis of the cells were also incubated with gp120 affinity column overnight. Following the overnight incubation, the columns were washed with PDS and eluted with buffer (SDS and bME). The elutates were analyzed by SDS-PAGE gel screening (coomassie blue staining).

Subsequently, the glycine-eluted material was incubated with labeled-gp120 (fluorescent tag). After incubation, the samples from various stages of purification (wash, elutate, etc.) were run using Water HPLC with a BioSi1250 column (BioRad)

Both the BIAcore tested and the elutate of gp120-affinity column tested samples of invasin-CD4 fusion protein expressed by the construct shown in FIG. 2J (SEQ ID NO:13) bound to gp120. Furthermore, complexes of this invasin-CD4 fusion protein with gp120 was also recognized by monoclonal antibody 48D, indicating that invasin-CD4 fusion proteins can expose cryptic (inducible). epitopes upon binding to gp120.

Example 4

Preparation of Env-Fusion Protein Complexes

Stable purified env-fusion protein (CD4-invasin) complexes are prepared with and without formaldehyde treatment. For example, to induce conformational changes in env, equimolar concentration of env (e.g. SF2 or SF162) and fusion proteins described herein are incubated together at 37° C. for one hour. At the cellular level, these interactions are transient. Therefore, at the end of incubation, half of the complexes are fixed with formaldehyde while the other half remain untreated. Both the treated and untreated complexes are separated on Superdex-200 column. Purified fractions are analyzed on an HPLC column and on SDS-PAGE. The purified complexes contained both env and fusion proteins together. Furthermore, these complexes are expected to be homogeneous and will not contain more than 2-3% of free fusion protein.

The ability of Env to complex to the fusion proteins described herein is monitored by the induction of CD4 inducible epitopes recognized by MAbs 17b and 48d using standard techniques. In particular, purified chimerae produced in the SF162 Env background, then, are characterized by surface plasmon resonance (SPR) to evaluate exposure of CD41 epitopes and by co-receptor binding tests to evaluate their binding affinities. See, also Devico et al. (1996) *Virology* 218:258-263 and Zhang et al. (1999) *Biochemistry* 38(29): 9405-9416 which show SPR testing of another CD4 miniprotein and that the CD4 miniproteins are able to compete with sCD4 for binding to the same env site, and to induce envelope conformational changes, as detected by the monoclonal antibody 17b (Sullivan et al. (1998) *J Virol* 72(8):6332-6338). This antibody recognizes an epitope located near the gp120 V3 loop and consisting mainly of the conserved stem of V1/V2, which is probably masked by the flanking V1/V2 and V3 loops (Kwong et al. (1998) *Nature* (London) 393:648-659; Rizzuto et al. (1998) *Science* 280:1949-1953) but exposed in the env complexed to CD4. The effect of miniprotein addition on antibody maximum binding and association rate increase was small, probably reflecting its low env binding affinity, but specific and easily detected. These procedures are applicable to gp120, gp140 and gp160 monomers, oligomers and variants thereof (e.g., to preparation of stable purified fusion protein complexes). Such variants include, for example, deletions of beta sheets and V2N3 loop deletions in env, and the like.

Example 5

Neutralizing Antibody Production Using CD4-Invasin Fusion Protein-Env Complexes

Vaccines comprising compositions of the invention can be delivered by various routes as well known in the art, including, e.g., delivery of a polypeptide antigen and/or delivery of a polynucleotide expressing the polypeptide in one or more dosings. For example, the DNA prime/protein boost strategy allows for screening of multiple Env structures in rabbits and non-human primates with the potential for epitope presentation in situ in the host when delivered as DNA vaccines. DNA vaccination can comprise administration of naked DNA, DNA e.g., complexed to PLG particles, or DNA as part of a viral vector and can be followed with protein boosting. Electroporation or DNA vaccination by use of a viral vector and other methods described herein are used to efficiently deliver polynucleotides encoding the fusion proteins (CD4-invasin) and/or Env polypeptides to non-human mammals (e.g., primates).

A. Fusion Protein-Env Complexes

Groups of 4-5 or more rabbits each are immunized with fixed or unfixed Env-fusion protein (CD4-invasin) complexes at 0, 4, 12 and 24 weeks. Sera are collected biweekly and analyzed against, e.g., SF2 or SF162 gp120 in an ELISA. The results from these rabbit studies will reveal which animals mount a strong immune response against gp120. Thus, the results will reveal the rationally designed fusion proteins including a CD4 miniprotein and heterologous polypeptide sequences (e.g., invasin), that bind with high affinity to different envelope forms (including oligomeric and monomeric forms of SF162 with and without V2-deletes), induce conformational changes in these proteins and induce full exposition of conserved cryptic CD4 inducible epitopes and/or co-receptor binding sites. Thus, the fusion proteins may be useful in complex with envelope protein to expose envelope epitopes to neutralizing antibodies thus may find potential application in vaccine formulations. Complexes identified by these rabbit studies are then tested in macaques.

B. Env-Fusion Protein Constructs

Groups of 4-5 or more rabbits each are immunized with constructs encoding Env and a fusion protein as described herein, on a single construct, as a fusion, or on two separate constructs at 0, 4, 12 and 24 weeks. Sera are collected biweekly and analyzed in an ELISA. Constructs identified by these rabbit studies are then tested in macaques.

C. Monkeys

Groups of 5 or more monkeys are immunized with Env-fusion protein complexes or Env-fusion proteins constructs with adjuvant along with control groups of Env protein only and fusion molecules only. Complexes are made with monomeric and oligomeric forms of SF162 Env with and without V2-deletes and the antibody responses compared. Immunization schedules are at 0, 4, and 24 week immunizations. When warranted, an additional booster may be included at later time points.

Example 6

Unmasking Cryptic Epitopes of gp41 Subunit in Oligomeric Envelopes

CD4 minimal modules and fusions comprising these minimal modules (CD4-invasin fusions) can induce a conformational transformation of oligomeric (o-gp140) envelopes, unmasking cryptic epitopes, close to co-receptor sites in gp120 subunit and efficiently increase co-receptor binding affinity in different gp120 envelopes. The induction of this conformational transformation by the fusion molecules described herein, binding in the different oligomeric Env structures, is tested using SPR technology and 2F5 mAb or DP178 peptides (or congeners). The effect of addition of peptides from the N-terminal domain of CCR5 co-receptor, which have been shown to bind to gp120 is also examined.

If exposition of gp41 epitopes is demonstrated, the peptides are chemically coupled to the CD4-invasin fusion proteins, to produce novel bi-functional ligands, presenting increased potency in unmasking gp41 epitopes. Novel chimeric oligomeric envelopes, incorporating the bi-functional ligands are also produced chemically or genetically, and tested. Candidate envelope proteins with superior exposure of gp120 and gp41 cryptic epitopes are then tested in animals for the induction of neutralizing antibodies.

Example 7

Production of Monoclonal Antibodies Targeting Cryptic Conserved Epitopes of Env

Selected fusion proteins and complexes comprising these fusion proteins immunogens are injected in rats to prepare monoclonal antibodies, according to the standard procedures. Clones are screened in ELISA against CD4 miniprotein-gp120 complex, CD4 miniprotein-invasin fusion proteins complexed to o-gp140, o-gp140, gp120 and o-gp140 alone. Clones exhibiting highest affinity for complexes as compared to envelopes alone are further tested in Biacore. Clones scoring positive in Biacore against the CD4M33-gp120 and/or CD4M33-o-gp140 complexes are selected and used for bulk production of ascites fluids.

Example 8

Mucosal Challenge Following Administration of Env-CD4-Invasin Complexes

Evaluation of Env-CD4 mimetic complexes for their ability to confer protection against heterologous challenge in rhesus macaques is tested. Specifically, combinations of these complexes with various adjuvants are administered to macaques and responses (e.g., virus load, antibody and/or T cell responses) of the animals evaluated pre- and post-challenge with mucosally SHIV challenge. The results from both the pre-challenge (immunogenicity) and post-challenge arms should provide data that will reveal which candidate immunogens and deliveries warrant further evaluation in macaques. The potency and breadth of the observed immune responses are considered as well as protective efficacy.

A. Cellular Immune Responses

The cellular immune parameters monitored regularly include enumeration of antigen-specific T-helper responses (IFN-γ, IL-2 and IL-4) as measured by ELISpot and lymphocyte proliferation (LP) responses. The kinetics of T-cell responses will primarily be measured by enumerating the number of CD4+ and CD8+ T cells that secrete IFN-γ in response to specific peptides. If particular (matching) MHC specific tetramer reagents are not available, then the majority of assays will by performed by CD8+ ELISpot assays with overlapping pools of peptides, from which epitope specificities are determined. Classical bulk lysis (Chromium release) assays are performed as confirmatory assays. Additional supplementary assays such as flow cytometric assays to measure antigen-specific intracellular cytokines in T-cell subsets, and tetramer analysis to measure antigen-specific CD8+ T-cell populations in animals with MHC specificities that match available tetramers will also be performed on a subset of animals.

Assays for the measurement of cellular immune responses in the mucosal will include ELISpot, measurements of antibody-secreting cells (ASC), and FACS analysis of antigen-specific intracellular cytokines in mucosal T-cells.

B. Humoral/Neutralizing Antibody Responses

Antibody responses and neutralization assays are performed as described above and/or samples are sent to outside vendor for evaluation (e.g., Virologic, Inc).

C. Measurements of Vaccine Efficacy Post-Challenge

The Env-CD4 mimetics complexes that give strong and broad neutralization, complemented by strong CD4 and CD8 T cell responses, are tested by homologous and heterologous systemic (IV) and mucosal (IR) challenges. Over the last ten years this has proven to be the most reliable challenge dose where protection can be achieved with all controls contacting disease. Challenge is performed 8 weeks after the final immunization, except during the final year of study when challenges are performed in parallel groups of monkeys when half of the designated groups are challenged at 8 months after the final immunization.

The post-challenge measurements of vaccine efficacy to be evaluated are summarized in Table 2. The plasma and PBMC are collected for analysis (e.g., virological and FACS) at two-week intervals for the first two months after challenge and at monthly intervals thereafter.

Plasma virus load analysis is performed as well as a detailed analysis of any persistent low copy proviral infection of PBMC or lymph node cells. Detailed FACS analysis provide evidence of T-cell activation and/or CD4+ T cell loss and disease progression. Immunoblot assays and ELISA for non-vaccine viral antigens are used to determine whether seroconversion has occurred.

Protected animals are identified after taking all these parameters into account. "Protection against infection" is defined as no indication of virus infection by any of the virologic (and serologic) sensitive assays listed in Table 2. "Partial protection" is defined by significant reductions in the virus load as measured by quantitative virus isolation, levels of viral RNA, frequency of detection of proviral DNA in PBMC and lymph nodes (LN). "Protection from disease" is defined primarily by reductions in the decline of CD4+ T cells, fewer or less severe signs and symptoms, survival, and secondarily, by reductions in virus load, and the robustness of the post-challenge immune responses.

TABLE 2

Post-Challenge Measurements of Vaccine Efficacy

| Measurements of Virus Load | Immune Status/Disease Progression |
|---|---|
| Plasma RNA (quantitative PCR) | FACS (CD3, CD4, CD8, CD16, HLA-DR, CD20) |
| Proviral DNA (nested PCR/PBMC and LN) | Immunoblot and ELISA (seroconversion) |

TABLE 2-continued

Post-Challenge Measurements of Vaccine Efficacy

| Measurements of Virus Load | Immune Status/Disease Progression |
|---|---|
| Quantitative virus isolation (PBMC) | Clinical signs and symptoms |
| | Ag specific IFN-γ, IL-2, IL-4, ELISPot ICS for IL-2 loss in CD4 subsets |

The relative merit of a vaccine regimen for future study are decided based on the outcome of the challenges and the observed potency, breadth, and durability of the immune responses pre- and post-challenge. In addition to the magnitude of the antigen-specific IL-2 responses (ELISPot) before challenge, the loss of Ag-specific IL-2 producing CD4 T-cell subsets as measured by ICS is prognostic of failure to contain/control virus load after challenge (see, also, Ogg et al. (1998) *Science* 279(5359):2103-2106; Oldstone et al. (1997) *Virol.* 234(2):179-185).

What is claimed is:

1. A fusion protein comprising a CD4 minimal module that binds to a Human Immunodeficiency Virus (HIV) Envelope (Env) polypeptide, and one or more heterologous polypeptide sequences, wherein the tertiary structure of the fusion protein exhibits structural similarity to native CD4;
   wherein at least one heterologous polypeptide sequence is a *Y. pseudotuberculosis* invasin polypeptide;
   wherein the CD4 minimal module maintains the structural conformation of a CDR2-like loop;
   wherein binding of the CD4 minimal module to the Env polypeptide induces exposure of a cryptic Env epitope in or near the CD4-binding site or in or near the chemokine receptor-binding site.

2. The fusion protein of claim 1, wherein the CD4 minimal module comprises residues 15 to 85 of CD4 (SEQ ID NO:4).

3. The fusion protein of claim 1, wherein the invasin polypeptide is selected from the group consisting of one or more of SEQ ID NOS:5-13.

4. The fusion protein of claim 3, comprising, from N-terminus to C-terminus, SEQ ID NO:5, SEQ ID NO:4, SEQ ID NO:6 and SEQ ID NO:7.

5. The fusion protein of claim 4, further comprising C-terminal to SEQ ID NO:7, one or more of SEQ ID NOS:8, 9 and 10.

6. The fusion protein of claim 1, further comprising an additional heterologous polypeptide.

7. The fusion protein of claim 6, wherein the additional heterologous polypeptide is selected from the group consisting of a viral polypeptide, an immunomodulatory polypeptide and a bacterial polypeptide.

8. The fusion protein of claim 7, wherein the additional heterologous polypeptide is a viral polypeptide and the virus is HIV.

9. The fusion protein of claim 8, wherein the viral polypeptide is an HIV Env polypeptide.

10. The fusion protein of claim 9, wherein the HIV Env polypeptide comprises Gp140, oligomeric gp140 (ogp140) or gp120.

11. An immunogenic composition comprising the fusion protein of claim 1.

12. The immunogenic composition according to claim 11, further comprising an adjuvant.

* * * * *

SEQUENCE LISTING

<160> NUMBER OF SEQ ID NOS: 13

<210> SEQ ID NO 1
<211> LENGTH: 268
<212> TYPE: PRT
<213> ORGANISM: Homo sapien

<400> SEQUENCE: 1

Lys Lys Val Val Gly Lys Lys Gly Asp Thr Val Thr Cys Thr Ala Ser
1               5                   10                  15

Lys Lys Ser His Trp Lys Asn Ser Asn Lys Gly Asn Gly Ser Thr Lys
            20                  25                  30

Gly Ser Lys Asn Asp Arg Ala Asp Ser Arg Arg Ser Trp Asp Gly Asn
        35                  40                  45

Lys Asn Lys Asp Ser Asp Thr Tyr Cys Val Asp Lys Val Val Gly Thr
    50                  55                  60

Ala Asn Ser Asp Thr His Gly Ser Thr Thr Ser Gly Ser Ser Ser Val
65                  70                  75                  80

Cys Arg Ser Arg Gly Lys Asn Gly Gly Lys Thr Ser Val Ser Asp Ser
                85                  90                  95

Gly Thr Trp Thr Cys Thr Val Asn Lys Lys Val Lys Asp Val Val Ala
            100                 105                 110

Lys Ala Ser Ser Val Tyr Lys Lys Gly Val Ser Ala Thr Val Lys Thr
        115                 120                 125

Gly Ser Gly Trp Trp Ala Arg Ala Ser Ser Ser Lys Ser Trp Thr Asp
    130                 135                 140

Lys Asn Lys Val Ser Val Lys Arg Val Thr Asp Lys Met Gly Lys Lys
145                 150                 155                 160

His Thr Ala Tyr Ala Gly Ser Gly Asn Thr Ala Ala Lys Thr Gly Lys
                165                 170                 175

His Val Asn Val Val Met Arg Ala Thr Lys Asn Thr Cys Val Trp Gly
            180                 185                 190

Thr Ser Lys Met Ser Lys Asn Lys Ala Lys Val Ser Lys Arg Lys Ala
        195                 200                 205

Val Trp Val Asn Ala Gly Met Trp Cys Ser Asp Ser Gly Val Ser Asn
    210                 215                 220

Lys Val Thr Trp Ser Thr Val Met Ala Val Gly Gly Val Ala Gly Gly
225                 230                 235                 240

Gly Cys Val Arg Cys Arg His Arg Arg Ala Arg Met Ser Lys Arg
                245                 250                 255

Ser Lys Lys Thr Cys Cys His Arg Lys Thr Cys Ser
            260                 265

<210> SEQ ID NO 2

```
<211> LENGTH: 685
<212> TYPE: PRT
<213> ORGANISM: Yersinia tuberculosis

<400> SEQUENCE: 2

Met Met Val Ser Arg Asn Ala Gly Met Ser Met Tyr Asn Lys Ser Asn
1               5                   10                  15

Ser Arg Val Cys Cys Gly Met Met Ala Gly Ala Ser Lys Tyr Asp Ala
            20                  25                  30

Asn Ala Val Tyr Ser Val Ser Ser Ala Asn His Asn Asn Met Ser
            35                  40                  45

Ser Asn Ser Ala Ser Asp Thr Arg Asn Ala Ala Asp Arg Ala Asn Lys
50                  55                  60

Thr Ala Val Asn Lys Met Ser Thr Gly Ala Arg Ala Ala Ser Gly Arg
65                  70                  75                  80

Ala Ser Asp Val Ala His Ser Met Val Gly Asp Ala Val Asn Lys Trp
                85                  90                  95

Asn Arg Gly Thr Ala Val Asn Asn Asp Lys Asn Ser Lys Ser Ser Asp
            100                 105                 110

Trp Ala Trp Tyr Asp Ser Ala Ser Ser Gly Arg Asn Lys Asp Ser Arg
            115                 120                 125

Asn Thr Asn Gly Val Gly Arg Thr Asn Gly Trp Tyr Gly Asn Thr Tyr
130                 135                 140

Asp Asn Asp Thr Gly His Asn His Arg Gly Gly Ala Ala Trp Thr Asp
145                 150                 155                 160

Tyr Ala Ala Asn Gly Tyr Arg Asn Gly Trp His Ser Ser Arg Asp Ser
                165                 170                 175

Asp Tyr Lys Arg Ala Thr Gly Gly Asp Arg Ala Asn Ala Tyr Ala Gly
            180                 185                 190

Gly Lys Met Tyr Tyr Thr Gly Arg Val Ala Gly Lys Asp Asn Arg Asn
            195                 200                 205

Tyr Ala Val Thr Ala Gly Asn Tyr Thr Val Thr Val Gly Val Asp Arg
210                 215                 220

Met Gly Lys Ser Ser Lys His Thr Trp Asn Met Asn Tyr Arg Gly Ser
225                 230                 235                 240

Ser Ser Ser Ala Val Ala Gly Thr Arg Ala Ser Arg Tyr Asn Val Asp
                245                 250                 255

Arg Asn Asn Asn Val Tyr Lys Val Val Lys Thr Ser Ala Thr Ser Gly
            260                 265                 270

Gly Val Tyr Val Asn Ala Val Gly Ala Ser Ala Val Arg Val Trp Ser
            275                 280                 285

Asp Ala Ala Ala Gly Gly Thr Thr Ser Thr Thr Asn Val Tyr Lys Arg
290                 295                 300

Thr Ala Val Ser Arg Val Thr Asp Asp Thr Ala Asn Tyr Ser Ser Ala
305                 310                 315                 320

Ala Val Asp His Gly Asn Arg Ser Asn Ser Thr Ser Val Thr Val Thr
                325                 330                 335

Thr Ala Ala Val Gly Asp Gly Ala Ala Asn Gly Lys Thr Ala Thr Val
            340                 345                 350

Thr Val Ala Asp Gly Lys Ala Gly Val Val Thr Thr Asn Asn Gly Ala
            355                 360                 365

Asn Lys Thr Lys Thr Asp Ala Asn Gly Val Ala Arg Ala Thr Asn Thr
370                 375                 380

Thr Asp Gly Val Thr Val Val Ala Val Gly Arg Ser Val Asp Thr
385                 390                 395                 400
```

His Val Lys Gly Thr Ala Ala Asp Lys Ser Thr Ala Ala Val Thr Ser
        405                 410                 415
Ala Asp Gly Met Ala Ser Thr Thr Lys Asp Thr Tyr Gly Asp Ala Gly
        420                 425                 430
Ala Asn Val Ala Asp Thr Thr Gly Asn Met Gly Val Thr Asp His Asn
        435                 440                 445
Asp Gly Thr Tyr Ser Ala Thr Ser Thr Thr Gly Val Ala Thr Val Thr
        450                 455                 460
Val Lys Val Asp Gly Ala Ala Ser Val Ser Thr Val Asn Thr Ala
465                 470                 475                 480
Asp Asp Ala Gly Arg Ser Ser Thr Val Ser Thr Ala Asp Gly Thr
                485                 490                 495
Met Ser Ser Thr Ser Val Val Asp Lys Asn Gly His Ser Gly Met Gly
        500                 505                 510
Ser Thr Asn Gly Val Val Ser Ser Thr Asp Ser Tyr Thr Ala Thr Val
        515                 520                 525
Val Gly Asn Ser Val Gly Asp Val Thr Thr Val Asp Thr Ser Thr Lys
        530                 535                 540
Lys Ser Val Thr Thr Gly Val Asn Gly Asn Ala Thr Asp Lys Gly Lys
545                 550                 555                 560
Thr Lys Asn Ala Thr Met Asp Asn Asp Val Ala Asn Asn Thr Tyr Trp
                565                 570                 575
Ser Ser Ser Thr Asn Val Ser Val Asn Asp Gly Val Thr Thr Tyr Thr
        580                 585                 590
Tyr Ser Val Ala Val Thr Ala Lys Ser Lys Lys Ser Tyr Ser Val Ser
        595                 600                 605
Tyr Arg Tyr Asn Arg Trp Tyr Asp Gly Gly Arg Ser Val Ser Ser Ala
        610                 615                 620
Ser Arg Cys Gly Ser Asp Met Ser Ala Val Ser Ser Arg Ala Thr Asn
625                 630                 635                 640
Gly Thr Arg Ala Asp Gly Thr Trp Gly Trp Gly Ser Thr Ala Tyr Ser
                645                 650                 655
Ser Asp Trp Ser Gly Tyr Trp Val Lys Lys Thr Ser Thr Asp Thr Met
        660                 665                 670
Asn Met Asp Thr Gly Ala Gly Ala Tyr Ala Cys Ala Ser
        675                 680                 685

<210> SEQ ID NO 3
<211> LENGTH: 2961
<212> TYPE: DNA
<213> ORGANISM: Unknown
<220> FEATURE:
<223> OTHER INFORMATION: Invasin-encoding polynucleotide

<400> SEQUENCE: 3
atgatggttt tccagccaat cagtgagttt ctcttgataa ggaatgcggg aatgtctatg      60
tattttaata aaataatttc atttaatatt atttcacgaa tagttatttg tatcttttg     120 atatgtggaa tgttcatggc tggggcttca gaaaaatatg atgctaacgc accgcaacag     180
gtccagcctt attctgtctc ttcatctgca tttgaaaatc tccatcctaa taatgaaatg     240
gagagttcaa tcaatccctt ttccgcatcg gatacagaaa gaaatgctgc aataatagat     300
cgcgccaata aggagcagga gactgaagcg gtgaataaga tgataagcac cggggccagg     360
ttagctgcat caggcagggc atctgatgtt gctcactcaa tggtgggcga tgcggttaat     420
caagaaatca acagtggtt aaatcgattc ggtacggctc aagttaatct gaattttgac     480

```
aaaaatttt   cgctaaaaga   aagctctctt   gattggctgg   ctccttggta   tgactctgct    540
tcattcctct   ttttagtca   gttaggtatt   cgcaataaag   acagccgcaa   cacacttaac    600
cttggcgtcg   ggatacgtac   attggagaac   ggttggctgt   acggacttaa   tacttttat     660 gataatgatt   tgaccggcca   caaccaccgt   atcggtcttg   gtgccgaggc   ctggaccgat    720
tatttacagt   tggctgccaa   tgggtatttt   cgcctcaatg   gatggcactc   gtcgcgtgat    780
ttctccgact   ataaagagcg   cccagccact   ggggggggatt   tgcgcgcgaa   tgcttattta    840
cctgcactcc   cacaactggg   ggggaagttg   atgtatgagc   aatacaccgg   tgagcgtgtt   900
gctttatttg   gtaaagataa   tctgcaacgc   aacccttatg   ccgtgactgc   cgggatcaat   960 tacaccccg    tgcctctact   cactgtcggg   gtagatcagc   gtatgggggaa  aagcagtaag   1020 catgaaacac   agtggaacct   ccaaatgaac   tatcgcctgg   gcgagagttt   tcagtcgcaa   1080
cttagcccct   cagcggtggc   aggaacacgt   ctactggcgg   agagccgcta   taaccttgtc   1140
gatcgtaaca   ataatatcgt   gttggagtat   cagaaacagc   aggtggttaa   actgacatta   1200
tcgccagcaa   ctatctccgg   cctgccgggt   caggtttatc   aggtgaacgc   acaagtacaa   1260
ggggcatctg   ctgtaaggga   aattgtctgg   agtgatgccg   aactgattgc   cgctggcggc   1320
acattaacac   cactgagtac   cacacaattc   aacttggttt   taccgcctta   taaacgcaca   1380
gcacaagtga   gtcgggtaac   ggacgacctg   acagccaact   tttattcgct   tagtgcgctc   1440
gcggttgatc   accaaggaaa   ccgatctaac   tcattcacat   tgagcgtcac   cgttcagcag   1500
cctcagttga   cattaacggc   ggccgtcatt   ggtgatggcg   caccggctaa   tgggaaaact   1560
gcaatcaccg   ttgagttcac   cgttgctgat   tttgagggga   aaccctttagc  cgggcaggag   1620 gtggtgataa   ccaccaataa   tggtgcgcta   ccgaataaaa   tcacggaaaa   gacagatgca   1680
aatggcgtcg   cgcgcattgc   attaaccaat   acgacagatg   gcgtgacggt   agtcacagca   1740
gaagtggagg   ggcaacggca   aagtgttgat   acccactttg   ttaagggtac   tatcgcggcg   1800
gataaatcca   ctctggctgc   ggtaccgaca   tctatcatcg   ctgatggtct   aatggcttca   1860
accatcacgt   tggagttgaa   ggataccctat  ggggacccgc   aggctggcgc   gaatgtggct   1920
tttgacacaa   ccttaggcaa   tatgggcgtt   atcacggatc   acaatgacgg   cacttatagc   1980
gcaccattga   ccagtaccac   gttgggggta   gcaacagtaa   cggtgaaagt   ggatggggct   2040
gcgttcagtg   tgccgagtgt   gacggttaat   ttcacggcag   atcctattcc   agatgctggc   2100
cgctccagtt   tcaccgtctc   cacaccggat   atcttggctg   atggcacgat   gagttccaca   2160 ttatccttttg  tccctgtcga   taagaatggc   cattttatca   gtgggatgca   gggcttgagt   2220
tttactcaaa   acgtgtgcc   ggtgagtatt   agccccatta   ccgagcagcc   agatagctat   2280
accgcgacgg   tggttgggaa   tagtgtcggt   gatgtcacaa   tcacgccgca   ggttgatacc   2340
ctgatactga   gtacattgca   gaaaaaaata   tccctattcc   cggtacctac   gctgaccggt   2400
attctggtta   acgggcaaaa   tttcgctacg   gataaagggt   tcccgaaaac   gatctttaaa   2460
aacgccacat   tccagttaca   gatggataac   gatgttgcta   ataatactca   gtatgagtgg   2520
tcgtcgtcat   tcacacccaa   tgtatcggtt   aacgatcagg   gtcaggtgac   gattacctac   2580
caaacctata   gcgaagtggc   tgtgacggcg   aaaagtaaaa   aattcccaag   ttattcggtg   2640
agttatcggt   tctacccaaa   tcggtggata   tacgatggcg   gcagatcgct   ggtatccagt   2700
ctcgaggcca   gcagacaatg   ccaaggttca   gatatgtctg   cggttcttga   atcctcacgt   2760
gcaaccaacg   gaacgcgtgc   gcctgacggg   acattgtggg   gcgagtgggg   gagcttgacc   2820
gcgtatagtt   ctgattggca   atctggtgaa   tattgggtca   aaaagaccag   cacggatttt   2880
```

```
gaaaccatga atatggacac aggcgcactg caaccagggc ctgcatactt ggcgttcccg    2940
ctctgtgcgc tgtcaatata a                                              2961
```

<210> SEQ ID NO 4
<211> LENGTH: 46
<212> TYPE: PRT
<213> ORGANISM: Homo sapien

<400> SEQUENCE: 4

Thr Cys Thr Ala Ser Lys Lys Ser His Trp Lys Asn Ser Asn Lys Gly
1               5                   10                  15

Asn Gly Ser Thr Lys Gly Ser Lys Asn Asp Arg Ala Asp Ser Arg Arg
            20                  25                  30

Ser Trp Asp Gly Asn Lys Asn Lys Asp Ser Asp Thr Tyr Cys
        35                  40                  45

<210> SEQ ID NO 5
<211> LENGTH: 9
<212> TYPE: PRT
<213> ORGANISM: Yersinia tuberculosis

<400> SEQUENCE: 5

Gly Ser Thr Asn Gly Val Val Ser Ser
1               5

<210> SEQ ID NO 6
<211> LENGTH: 9
<212> TYPE: PRT
<213> ORGANISM: Yersinia tuberculosis

<400> SEQUENCE: 6

Gly Arg Ser Val Asp Thr His Val Lys
1               5

<210> SEQ ID NO 7
<211> LENGTH: 68
<212> TYPE: PRT
<213> ORGANISM: Yersinia tuberculosis

<400> SEQUENCE: 7

Thr Thr Ala Ala Val Gly Asp Gly Ala Ala Asn Gly Lys Thr Ala Thr
1               5                   10                  15

Val Thr Val Ala Asp Gly Lys Ala Gly Val Val Thr Thr Asn Asn Gly
            20                  25                  30

Ala Asn Lys Thr Lys Thr Asp Ala Asn Gly Val Ala Arg Ala Thr Asn
        35                  40                  45

Thr Thr Asp Gly Val Thr Val Thr Ala Val Gly Arg Ser Val Asp
    50                  55                  60

Thr His Val Lys
65

<210> SEQ ID NO 8
<211> LENGTH: 78
<212> TYPE: PRT
<213> ORGANISM: Yersinia tuberculosis

<400> SEQUENCE: 8

Gly Thr Ala Ala Asp Lys Ser Thr Ala Val Thr Ser Ala Asp Gly
1               5                   10                  15

Met Ala Ser Thr Thr Lys Asp Thr Tyr Gly Asp Ala Gly Ala Asn Val
            20                  25                  30

-continued

Ala Asp Thr Thr Gly Asn Met Gly Val Thr Asp His Asn Asp Gly Thr
            35                  40                  45

Tyr Ser Ala Thr Ser Thr Thr Gly Val Ala Thr Val Thr Val Lys Val
 50                  55                  60

Asp Gly Ala Ala Ser Val Ser Val Thr Val Asn Thr Ala Asp
65                  70                  75

<210> SEQ ID NO 9
<211> LENGTH: 66
<212> TYPE: PRT
<213> ORGANISM: Yersinia tuberculosis

<400> SEQUENCE: 9

Asp Ala Gly Arg Ser Ser Thr Val Ser Thr Asp Ala Asp Gly Thr Met
1               5                   10                  15

Ser Ser Thr Ser Val Val Asp Lys Asn Gly His Ser Gly Met Gly Ser
            20                  25                  30

Thr Asn Gly Val Val Ser Ser Thr Asp Ser Tyr Thr Ala Thr Val Val
            35                  40                  45

Gly Asn Ser Val Gly Asp Val Thr Thr Val Asp Thr Ser Thr Lys Lys
 50                  55                  60

Ser Val
65

<210> SEQ ID NO 10
<211> LENGTH: 66
<212> TYPE: PRT
<213> ORGANISM: Yersinia tuberculosis

<400> SEQUENCE: 10

Thr Thr Gly Val Asn Gly Asn Ala Thr Asp Lys Gly Lys Thr Lys Asn
1               5                   10                  15

Ala Thr Met Asp Asn Asp Val Ala Asn Asn Thr Tyr Trp Ser Ser Ser
            20                  25                  30

Thr Asn Val Ser Val Asn Asp Gly Val Thr Thr Tyr Thr Tyr Ser Val
            35                  40                  45

Ala Val Thr Ala Lys Ser Lys Lys Ser Tyr Ser Val Ser Tyr Arg Tyr
 50                  55                  60

Asn Arg
65

<210> SEQ ID NO 11
<211> LENGTH: 146
<212> TYPE: PRT
<213> ORGANISM: Yersinia tuberculosis

<400> SEQUENCE: 11

Thr Thr Ala Ala Val Gly Asp Gly Ala Ala Asn Gly Lys Thr Ala Thr
1               5                   10                  15

Val Thr Val Ala Asp Gly Lys Ala Gly Val Val Thr Thr Asn Asn Gly
            20                  25                  30

Ala Asn Lys Thr Lys Thr Asp Ala Asn Gly Val Ala Arg Ala Thr Asn
            35                  40                  45

Thr Thr Asp Gly Val Thr Val Thr Ala Val Gly Arg Ser Val Asp
 50                  55                  60

Thr His Val Lys Gly Thr Ala Ala Asp Lys Ser Thr Ala Ala Val Thr
65                  70                  75                  80

Ser Ala Asp Gly Met Ala Ser Thr Thr Lys Asp Thr Tyr Gly Asp Ala

```
                    85                  90                  95
Gly Ala Asn Val Ala Asp Thr Thr Gly Asn Met Gly Val Thr Asp His
            100                 105                 110
Asn Asp Gly Thr Tyr Ser Ala Thr Ser Thr Thr Gly Val Ala Thr Val
            115                 120                 125
Thr Val Lys Val Asp Gly Ala Ala Ser Val Ser Val Thr Val Asn Thr
            130                 135                 140
Ala Asp
145

<210> SEQ ID NO 12
<211> LENGTH: 212
<212> TYPE: PRT
<213> ORGANISM: Yersinia tuberculosis

<400> SEQUENCE: 12

Thr Thr Ala Ala Val Gly Asp Gly Ala Ala Asn Gly Lys Thr Ala Thr
1               5                   10                  15
Val Thr Val Ala Asp Gly Lys Ala Gly Val Val Thr Thr Asn Asn Gly
            20                  25                  30
Ala Asn Lys Thr Lys Thr Asp Ala Asn Gly Val Ala Arg Ala Thr Asn
        35                  40                  45
Thr Thr Asp Gly Val Thr Val Val Thr Ala Val Gly Arg Ser Val Asp
    50                  55                  60
Thr His Val Lys Gly Thr Ala Ala Asp Lys Ser Thr Ala Ala Val Thr
65                  70                  75                  80
Ser Ala Asp Gly Met Ala Ser Thr Thr Lys Asp Thr Tyr Gly Asp Ala
                85                  90                  95
Gly Ala Asn Val Ala Asp Thr Thr Gly Asn Met Gly Val Thr Asp His
            100                 105                 110
Asn Asp Gly Thr Tyr Ser Ala Thr Ser Thr Thr Gly Val Ala Thr Val
            115                 120                 125
Thr Val Lys Val Asp Gly Ala Ala Ser Val Ser Val Thr Val Asn Thr
            130                 135                 140
Ala Asp Asp Ala Gly Arg Ser Ser Thr Val Ser Thr Asp Ala Asp Gly
145                 150                 155                 160
Thr Met Ser Ser Thr Ser Val Val Asp Lys Asn Gly His Ser Gly Met
                165                 170                 175
Gly Ser Thr Asn Gly Val Val Ser Ser Thr Asp Ser Tyr Thr Ala Thr
            180                 185                 190
Val Val Gly Asn Ser Val Gly Asp Val Thr Thr Val Asp Thr Ser Thr
            195                 200                 205
Lys Lys Ser Val
        210

<210> SEQ ID NO 13
<211> LENGTH: 278
<212> TYPE: PRT
<213> ORGANISM: Yersinia tuberculosis

<400> SEQUENCE: 13

Thr Thr Ala Ala Val Gly Asp Gly Ala Ala Asn Gly Lys Thr Ala Thr
1               5                   10                  15
Val Thr Val Ala Asp Gly Lys Ala Gly Val Val Thr Thr Asn Asn Gly
            20                  25                  30
Ala Asn Lys Thr Lys Thr Asp Ala Asn Gly Val Ala Arg Ala Thr Asn
        35                  40                  45
```

```
Thr Thr Asp Gly Val Thr Val Val Thr Ala Val Gly Arg Ser Val Asp
        50              55              60
Thr His Val Lys Gly Thr Ala Ala Asp Lys Ser Thr Ala Ala Val Thr
 65              70              75                          80
Ser Ala Asp Gly Met Ala Ser Thr Thr Lys Asp Thr Tyr Gly Asp Ala
                 85              90                      95
Gly Ala Asn Val Ala Asp Thr Thr Gly Asn Met Gly Val Thr Asp His
            100             105             110
Asn Asp Gly Thr Tyr Ser Ala Thr Ser Thr Thr Gly Val Ala Thr Val
        115             120             125
Thr Val Lys Val Asp Gly Ala Ala Ser Val Ser Val Thr Val Asn Thr
        130             135             140
Ala Asp Asp Ala Gly Arg Ser Ser Thr Val Ser Thr Asp Ala Asp Gly
145             150             155                         160
Thr Met Ser Ser Thr Ser Val Val Asp Lys Asn Gly His Ser Gly Met
            165             170             175
Gly Ser Thr Asn Gly Val Val Ser Ser Thr Asp Ser Tyr Thr Ala Thr
            180             185             190
Val Val Gly Asn Ser Val Gly Asp Val Thr Thr Val Asp Thr Ser Thr
        195             200             205
Lys Lys Ser Val Thr Thr Gly Val Asn Gly Asn Ala Thr Asp Lys Gly
210             215             220
Lys Thr Lys Asn Ala Thr Met Asp Asn Asp Val Ala Asn Asn Thr Tyr
225             230             235             240
Trp Ser Ser Ser Thr Asn Val Ser Val Asn Asp Gly Val Thr Thr Tyr
            245             250             255
Thr Tyr Ser Val Ala Val Thr Ala Lys Ser Lys Lys Ser Tyr Ser Val
            260             265             270
Ser Tyr Arg Tyr Asn Arg
            275
```